(12) United States Patent
Wall et al.

(10) Patent No.: US 7,896,841 B2
(45) Date of Patent: *Mar. 1, 2011

(54) INJECTION DEVICE FOR ADMINISTERING A VACCINE

(75) Inventors: Eric James Wall, Cincinnati, OH (US); Jarvis Ward, Cincinnati, OH (US); Christopher J. Nesbitt, Cincinnati, OH (US); Daniel Frederick Nesbitt, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 259 days.

This patent is subject to a terminal disclaimer.

(21) Appl. No.: 10/597,997

(22) PCT Filed: Feb. 17, 2005

(86) PCT No.: PCT/US2005/004996

§ 371 (c)(1),
(2), (4) Date: Jun. 21, 2007

(87) PCT Pub. No.: WO2005/079440

PCT Pub. Date: Sep. 1, 2005

(65) Prior Publication Data

US 2007/0276320 A1 Nov. 29, 2007

Related U.S. Application Data

(60) Provisional application No. 60/521,076, filed on Feb. 17, 2004.

(51) Int. Cl.
*A61M 5/20* (2006.01)
*A61M 5/32* (2006.01)
*A61M 5/00* (2006.01)
*A61M 5/31* (2006.01)

(52) U.S. Cl. .................. 604/135; 604/198; 604/239
(58) Field of Classification Search ............ 604/117, 604/131–139, 156, 157, 192–198, 239
See application file for complete search history.

(56) References Cited

U.S. PATENT DOCUMENTS 2,671,488 A 3/1954 Harnisch
(Continued)

FOREIGN PATENT DOCUMENTS

EP 0651667 B1 5/1995
WO WO 9317754 A1 9/1993
(Continued)

OTHER PUBLICATIONS

Scarfone, Richard J., et al., Pain of Local Anesthetics: Rate of Administration and Buffering, Annals of Emergency Medicine, Jan. 1998, 31.1, 36-40.
(Continued)

*Primary Examiner*—Nicholas D Lucchesi
*Assistant Examiner*—Nathan R Price
(74) *Attorney, Agent, or Firm*—Hasse & Nesbitt LLC; Daniel F. Nesbitt

(57) ABSTRACT

An injection device that self-administers a painless vaccine injections. The injection device (10) can be secured to the patient's skin via a separable base portion (12) of the housing of the device, which can be separated from the device when removing the housing and syringe assemblies for disposal. The injection device can provide a method for substantial amount of time performing the injection procedure, that is relatively simple and inexpensive to perform and operate, and that provides a relatively high degree of safety for both the medical personnel and for the patient. The injection device is configured for easy handling, and is manually-powered by the use of the hand or fingers of the medical technician. The device can also comprise a plurality of vaccine syringes at the same time with a single device.

18 Claims, 21 Drawing Sheets

U.S. PATENT DOCUMENTS

| | | |
|---|---|---|
| 3,066,670 A | 12/1962 | Stauffer |
| 3,572,336 A | 3/1971 | Hershberg |
| 3,605,742 A | 9/1971 | Tibbs |
| 3,702,608 A | 11/1972 | Tibbs |
| 4,031,889 A | 6/1977 | Pike |
| 4,043,333 A | 8/1977 | Munsch |
| 4,085,748 A | 4/1978 | Boyer |
| 4,194,505 A | 3/1980 | Schmitz |
| 4,196,732 A | 4/1980 | Wardlow |
| 4,214,584 A | 7/1980 | Smirnov et al. |
| 4,227,528 A | 10/1980 | Wardlow |
| 4,267,836 A | 5/1981 | Whitney et al. |
| 4,270,537 A | 6/1981 | Romaine |
| 4,326,517 A | 4/1982 | Whitney et al. |
| 4,340,048 A | 7/1982 | Eckenhoff |
| 4,373,526 A | 2/1983 | Kling |
| 4,512,767 A | 4/1985 | Denance |
| 4,552,561 A | 11/1985 | Eckenhoff et al. |
| 4,734,092 A | 3/1988 | Millerd |
| 4,753,651 A | 6/1988 | Eckenhoff |
| 4,886,499 A | 12/1989 | Cirelli et al. |
| 4,894,054 A | 1/1990 | Miskinyar |
| 4,955,871 A | 9/1990 | Thomas |
| 4,968,302 A | 11/1990 | Schluter et al. |
| 5,019,047 A | 5/1991 | Kriesel |
| 5,078,680 A | 1/1992 | Sarnoff |
| 5,137,516 A | 8/1992 | Rand et al. |
| 5,156,591 A | 10/1992 | Gross et al. |
| 5,167,632 A | 12/1992 | Eid et al. |
| 5,169,389 A | 12/1992 | Kriesel et al. |
| 5,205,820 A | 4/1993 | Kriesel |
| 5,236,419 A | 8/1993 | Seney |
| 5,267,963 A | 12/1993 | Bachynsky |
| 5,279,544 A | 1/1994 | Gross et al. |
| 5,279,558 A | 1/1994 | Kriesel |
| 5,318,557 A | 6/1994 | Gross |
| 5,336,188 A | 8/1994 | Kriesel |
| 5,352,201 A | 10/1994 | Jemmott |
| 5,354,287 A | 10/1994 | Wacks |
| 5,419,771 A | 5/1995 | Kriesel |
| 5,478,315 A | 12/1995 | Brothers et al. |
| 5,527,287 A | 6/1996 | Miskinyar |
| 5,527,288 A | 6/1996 | Gross et al. |
| 5,578,014 A | 11/1996 | Erez et al. |
| 5,616,123 A | 4/1997 | Cheikh |
| 5,616,128 A | 4/1997 | Meyer |
| 5,616,132 A | 4/1997 | Newman |
| 5,656,032 A | 8/1997 | Kriesel et al. |
| 5,681,291 A | 10/1997 | Galli |
| 5,693,018 A | 12/1997 | Kriesel et al. |
| 5,695,463 A | 12/1997 | Cherif-Cheikh |
| 5,704,520 A | 1/1998 | Gross |
| 5,704,911 A | 1/1998 | Parsons |
| 5,735,818 A | 4/1998 | Kriesel et al. |
| 5,762,634 A | 6/1998 | Davis |
| 5,785,688 A | 7/1998 | Joshi et al. |
| 5,791,466 A | 8/1998 | Tsals |
| 5,800,420 A | 9/1998 | Gross et al. |
| 5,807,375 A | 9/1998 | Gross et al. |
| 5,814,020 A | 9/1998 | Gross |
| 5,820,622 A | 10/1998 | Gross et al. |
| 5,848,990 A | 12/1998 | Cirelli et al. |
| 5,848,991 A | 12/1998 | Gross et al. |
| D404,366 S | 1/1999 | Gross et al. |
| D404,482 S | 1/1999 | Falk et al. |
| 5,858,001 A | 1/1999 | Tsals et al. |
| D405,524 S | 2/1999 | Falk et al. |
| 5,871,125 A | 2/1999 | Gross |
| 5,885,250 A | 3/1999 | Kriesel et al. |
| 5,921,963 A | 7/1999 | Erez et al. |
| 5,931,814 A | 8/1999 | Alex et al. |
| 5,957,895 A | 9/1999 | Sage et al. |
| 5,997,501 A | 12/1999 | Gross et al. |
| 6,042,565 A | 3/2000 | Hirschman et al. |
| 6,048,334 A | 4/2000 | Hirschman et al. |
| 6,077,247 A | 6/2000 | Marshall et al. |
| 6,086,562 A | 7/2000 | Jacobsen et al. |
| 6,132,395 A | 10/2000 | Landau et al. |
| 6,146,361 A | 11/2000 | DiBiasi et al. |
| 6,157,858 A | 12/2000 | Gross et al. |
| 6,186,982 B1 | 2/2001 | Gross et al. |
| 6,254,575 B1 | 7/2001 | Thorne, Jr. et al. |
| 6,264,629 B1 | 7/2001 | Landau |
| 6,312,412 B1 | 11/2001 | Saied |
| 6,319,224 B1 | 11/2001 | Stout et al. |
| 6,364,865 B1 | 4/2002 | Lavi et al. |
| 6,478,771 B1 | 11/2002 | Lavi et al. |
| 6,482,176 B1 | 11/2002 | Wich |
| 6,485,461 B1 | 11/2002 | Mason et al. |
| 6,494,865 B1 | 12/2002 | Alchas |
| 6,500,150 B1 | 12/2002 | Gross et al. |
| 6,530,900 B1 | 3/2003 | Daily et al. |
| 6,530,904 B1 | 3/2003 | Edwards et al. |
| 6,569,123 B2 | 5/2003 | Alchas et al. |
| 6,569,143 B2 | 5/2003 | Alchas et al. |
| 6,572,740 B2 | 6/2003 | Rosenblum et al. |
| 6,585,707 B2 | 7/2003 | Cabiri et al. |
| 6,589,210 B1 | 7/2003 | Rolfe |
| 6,589,229 B1 | 7/2003 | Connelly et al. |
| 6,595,947 B1 | 7/2003 | Mikszta et al. |
| 6,595,956 B1 | 7/2003 | Gross et al. |
| 6,605,064 B2 | 8/2003 | Katch |
| 6,645,180 B1 | 11/2003 | Hatch |
| 6,699,218 B2 | 3/2004 | Flaherty et al. |
| 6,702,779 B2 | 3/2004 | Connelly et al. |
| 6,749,587 B2 | 6/2004 | Flaherty |
| 6,939,330 B1 * | 9/2005 | McConnell-Montalvo et al. ............ 604/197 |
| 7,637,891 B2 * | 12/2009 | Wall .............. 604/131 |
| 7,670,314 B2 * | 3/2010 | Wall et al. ............. 604/135 |
| 2001/0012926 A1 | 8/2001 | Gross et al. |
| 2001/0039401 A1 | 11/2001 | Ferguson et al. |
| 2002/0055711 A1 | 5/2002 | Lavi et al. |
| 2002/0123719 A1 | 9/2002 | Lavi et al. |
| 2003/0023203 A1 | 1/2003 | Lavi et al. |
| 2003/0100862 A1 | 5/2003 | Edwards et al. |
| 2003/0105430 A1 | 6/2003 | Lavi et al. |
| 2003/0109827 A1 | 6/2003 | Lavi et al. |
| 2003/0135159 A1 | 7/2003 | Daily et al. |
| 2003/0144627 A1 * | 7/2003 | Woehr et al. ................ 604/110 |
| 2003/0187395 A1 | 10/2003 | Gabel et al. |
| 2004/0158207 A1 * | 8/2004 | Hunn et al. ............ 604/164.01 |

FOREIGN PATENT DOCUMENTS

| | | |
|---|---|---|
| WO | WO 9323096 A1 | 11/1993 |
| WO | WO 9423777 A1 | 10/1994 |
| WO | WO 9513838 A1 | 5/1995 |
| WO | WO 9532013 A1 | 11/1995 |
| WO | WO 9709078 A1 | 3/1997 |
| WO | WO 9710012 A1 | 3/1997 |
| WO | WO 9829662 A1 | 7/1998 |
| WO | WO 9959665 A1 | 11/1999 |
| WO | WO 0044437 A1 | 8/2000 |
| WO | WO 0202165 A2 | 1/2002 |

OTHER PUBLICATIONS

Edlisch, Richard F., et al., Performance of Disposable Needle Syringe Systems for Local Anesthesia, The Journal of Emergency Medicine, vol. 5 pp. 83-90, 1987.

Krause, Richard S., The Effect of Injection Speed on the Pain of Lidocaine Infiltration, Academic Emergency Medicine, Nov. 1997, vol. 4/No. 11, pp. 1032-1035.

Mitchell, Jane R. et al., The Effect of Injection Speed on the Perception of Intramuscular Injection Pain, AAOHN Journal, Jun. 2001, vol. 49, No. 6, pp. 286-292.

Graven-Nielsen, T., et al., In Vivo Model of Muscle Pain: Quantification of Intramuscular Chemical, Electrical, and Pressure Changes Associated with Saline-Induced Muscle Pain in Humans, Pain 69 (1997) pp. 137-143.

Graven-Nielsen, T., et al., Quantification of Local and Referred Muscle Pain in Humans after Sequential i.m. Injections of Hypertonic Saline, Pain 69 (1997) pp. 111-117.

CompuDent™, Milestone Scientific, 2002, www.milesci.com/cumpudent/index.php.

When Patient Care Needs to Be Pain Free . . . , PainFree pump, Sgarlato Labs, www.sgarlatolabs.com/pain_management.shtml, 2 pages; first publication date unknown.

Uniject™ Injection System Overview, PATH, 8 pages, www.path.org/technos/uniject-overview.htm; first publication date unknown.

Insulin Pump Technical Specifications, Debiotech S.A., Switzerland, www.debiotech.com/products/msys/ip_page_2.html; Mar. 4, 2002, 1 page.

Maillefer, Didier, et al., A High-Performance Silicon Micropump for Disposable Drug Delivery Systems, 0-7803-5998-4/01 IEEE, pp. 413-417, 2001.

The Medipad System Benefits and Applications, Elan Medical Technologies, 990M001, 2002, RevJan. 2003, 2 pages.

BD Medical brochure, Franklin Lakes, NJ, www.bd.com, 2003, 1 page.

National Collegiate Inventors & Innovators Alliance (NCIIA), Advanced E-Team, Grant Profile, Painless Injection Method and Device, publication Jan. 30, 2002, 1 page.

Beckton, Dickinson and Company brochure, BD™ Disposable Pen, 2000, 2 pages.

Beckton, Dickinson and Company brochure, BD™ Auto-Injector, 2000, 2 pages.

U.S. Appl. No. 10/605,187, filed Sep. 12, 2003, Wall et al.

U.S. Appl. No. 10/597,991, filed Aug. 15, 2006, Wall et al.

* cited by examiner

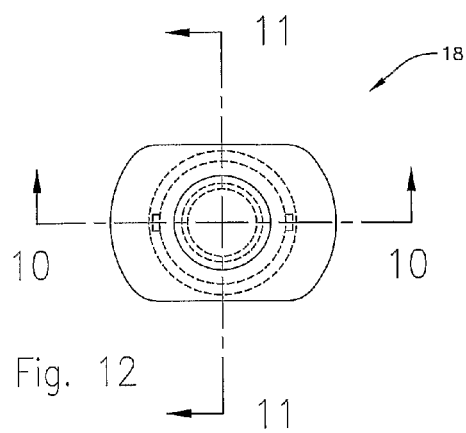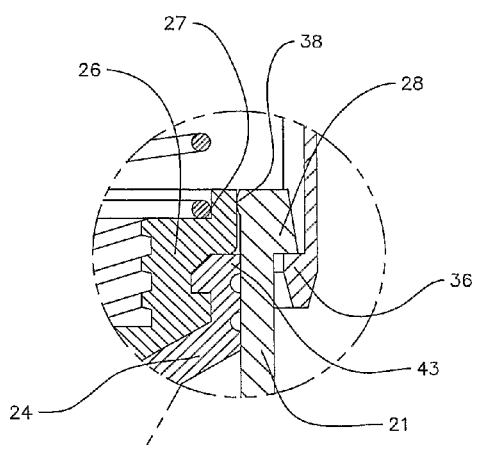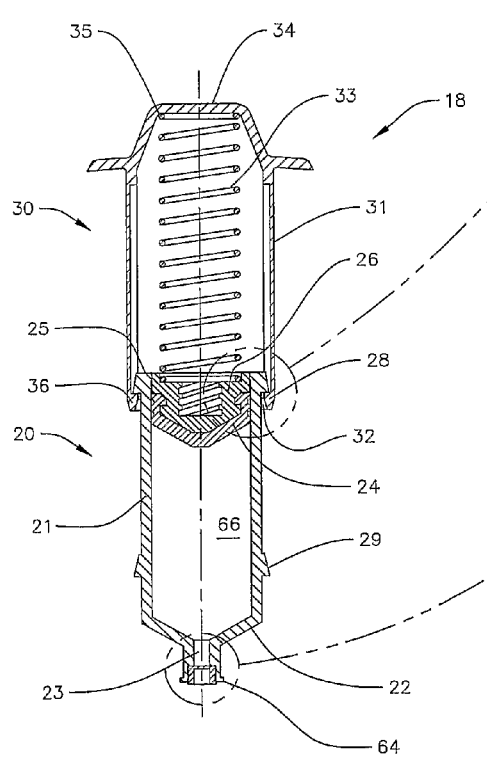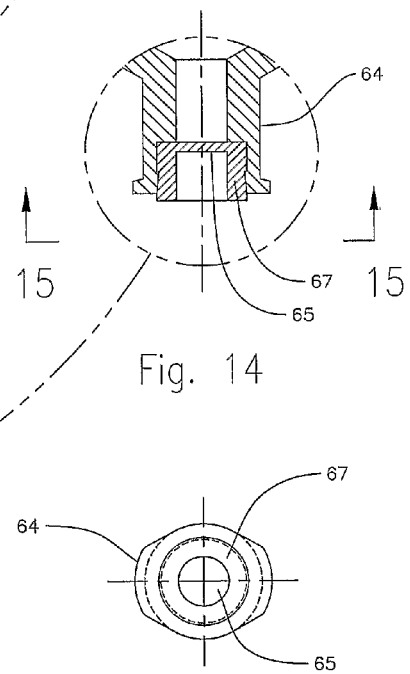

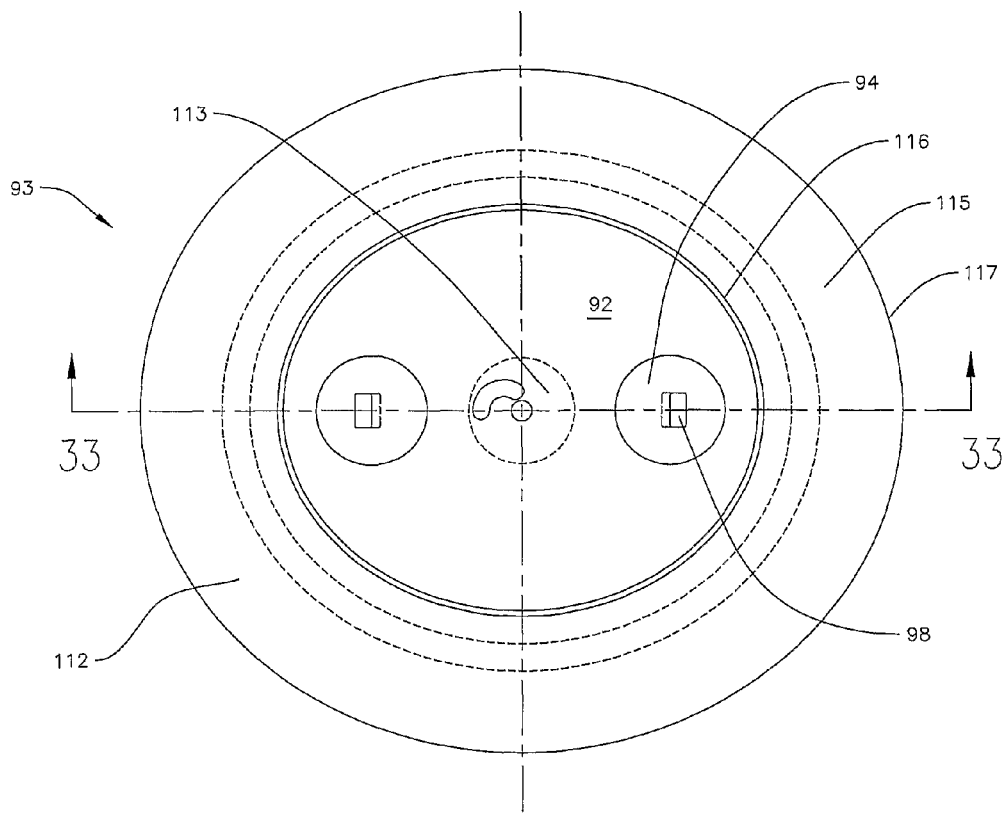
Fig. 32
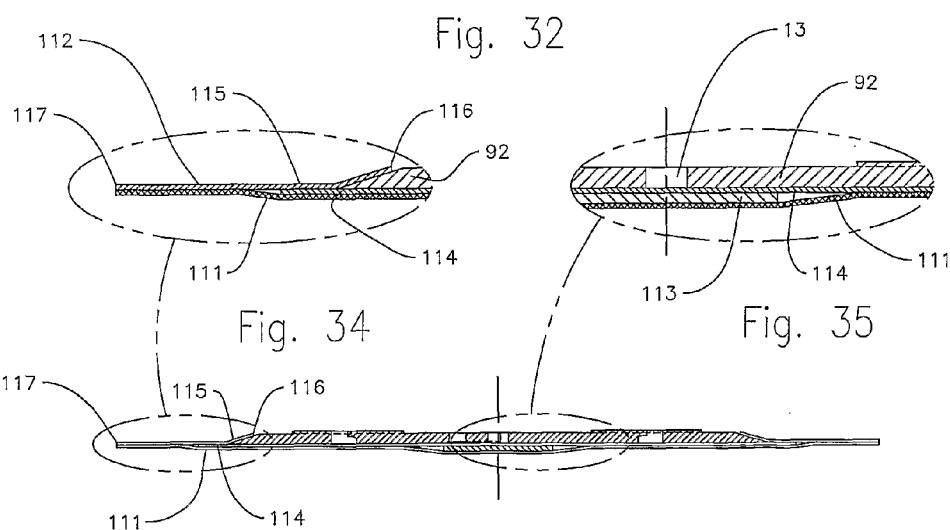
Fig. 34
Fig. 35
Fig. 33

INJECTION DEVICE FOR ADMINISTERING A VACCINE

CROSS REFERENCE TO RELATED APPLICATIONS

This is the National Stage of International Application PCT/US2005/004996, with an international filing date of Feb. 17, 2005, which claimed the benefit of U.S. Provisional Application No. 60/521,076, filed Feb. 17, 2004.

BACKGROUND

The present invention relates to the injection of vaccines and other medication and, more particularly, to an improved injection device that can be used in a method for administering vaccine injections painlessly for a patient.

Conventional medical injection devices for injecting medication into the muscle or tissue of a patient typically comprise some form of a manual hypodermic syringe. Generally speaking, a hypodermic syringe consists of a cylindrical barrel having a chamber that provides a reservoir for a liquid medication, a distal end adapted to be connected to a hollow hypodermic needle and for placing one end of the needle into flow communication with the medication contained within the chamber, and a proximal end adapted for receiving a stopper and plunger assembly. The stopper and plunger assembly includes a stopper effective for moving along the barrel chamber and an elongated plunger effective for causing movement of the stopper. The needle of the hypodermic syringe is manually inserted into the patient through the skin. The stopper is moved along the barrel chamber by applying axial force to the plunger, thereby forcing the liquid medication out of the barrel chamber, through the hypodermic needle and into the muscle or tissue of the patient.

Receiving an injection by such a conventional device can be a very traumatic experience, particularly for a child. The child's fears, and that of the child's parent, can become a significant medical problem if it leads to the child not receiving a required vaccination. These fears are predominately caused by pain that is associated with injections given by conventional injection devices and methods.

We have found that the pain associated with an injection is related to the size of the needle and the flow rate at which the medication is injected. It has been found that the amount of pain or discomfort experienced by a patient increases as the outside diameter of the needle increases. It is believed that high flow rates of medication injection (e.g., about 0.5-2 ml per second) into the patient can tear internal tissue and cause pain. The tearing of tissue is caused by the build-up of excessive pressure within the tissue when the surrounding tissue is unable to quickly absorb the injected medication.

While the injection of a medication at a relatively slow flow rate is more comfortable for the patient, the increased amount of time the syringe remains in the hand of the medical personnel can make the technique tiring for such personnel as well as the patient. In addition, small vibrations or disturbances of the needle caused by movement of the medical personnel or the patient can result in pain to the patient. It is known that the fluctuation of flow rate of the injection of medication being delivered by a hand-held syringe can vary greatly. It is extremely difficult, if not impossible, to deliver a steady, very slow flow of medication from a hand-operated syringe (the human thumb depressing the syringe plunger) over an extended amount of time.

It has also been found that the sight of the hypodermic needle by itself is often enough to cause many patients to become anxious and tense. This reaction in turn may cause the patient's muscles to become tight and hard, making needle penetration even more difficult and painful.

A number of methods and devices have been developed for reducing or eliminating the pain and discomfort associated with medical injections. One such method includes the application of a topical anesthetic to the injection site on the patient's skin prior to the injection, which itself can be painful. While this method has reduced some of the discomfort associated with injections, the topical anesthetic does not substantially penetrate the skin into the deeper skin and muscle tissue, and can take significant time (up to 45 minutes) to show effects. Substantial pain and discomfort with intramuscular injections can remain.

Another technique for reducing the pain and discomfort associated with medical injections includes the step of injecting an anesthetic at the site of the injection using a fine gauge needle, then inserting the larger medication hypodermic needle through the anesthetized skin to inject the medication at a constant and slow flow rate intramuscularly at the desired depth. Unfortunately, injecting an anesthetic into a patient is not always desirable and the technique is relatively expensive and impractical for many routine injection procedures.

In addition to reducing pain or discomfort to the patient, safety has also become a principal concern to medical personnel. Special precautions must be taken to avoid accidental needle sticks that could place a user at serious risk because of the danger from fluid borne pathogens. Despite the taking of special precautions, there still remains the possibility of an accidental needle contact and attendant injury. Accordingly, medical injection devices should operate to minimize the possibility of injury caused by accidental needle sticks.

In recent years, increased emphasis has been placed on establishing treatment protocols aimed at providing a patient as well as medical personnel with greater freedom of movement. To this end, there is a great deal of interest in the development of light weight and easy-to-use portable injection devices.

Accordingly, a need exists for substantially painless method and an apparatus for performing the method of injecting medication into a patient that does not require the use of an anesthetic, that does not require the medical personnel to spend a substantial amount of time performing a particular procedure, that is relatively simple, portable and inexpensive to perform and operate, that permits the patient a relatively high degree of movement during the injection, and that provides a relatively high degree of safety for both the medical personnel and for the patient.

SUMMARY OF INVENTION

The present invention relates to improvements in an injection device configured for self-administering painlessly an injectable liquid composition, such as a vaccine or medicament. The device can be used in a method for providing a substantially painless injection of the injectable liquid composition to a patient that does not require the use of an anesthetic, that does not require the medical personnel to spend a substantial amount of time performing the injection procedure, that is relatively simple and inexpensive to prepare and operate, and that provides a relatively high degree of safety for both the medical personnel and for the patient. The device can be manually powered, or can have self-contained power for at least inserting the injection needle into the patient.

The present invention also relates to an improved injection device for self-administering painlessly inter-muscular injections of an injectable liquid composition to a patient, comprising: a housing having a base portion; a needle positioned within the housing, the needle having an injection end having an outside diameter greater than 0.20 mm and less than about 0.38 mm, and being configured for extension to a position wherein the injection end extends through and beyond the base portion; a reservoir for the vaccine; and a means for liquid communication between the reservoir and the injection needle; a separable base associated with the base portion, comprising an adhesive on a skin-facing surface thereof and an opposed surface, and a means for separably affixing the separable base with the base portion.

The invention also relates to an improved device for injecting painlessly at least two injectable liquid compositions to a patient, comprising: a housing having a base for semi-permanent attachment to the skin of a patient, at least two injection needles disposed substantially perpendicular to the base and within the housing, each needle having an injection end and having an outside diameter greater than 0.20 mm and less than about 0.38 mm, and being configured for axial movement between a first position wherein the injection end is within the housing and a second position wherein the injection end extends outwardly from the base, and at least two reservoirs configured for liquid communication with the injection needles, a means for inserting each injection needle to its second position, a means for injecting the liquid composition from the reservoir to the injection end of the needle, and optionally a means for retracting each needle.

BRIEF DESCRIPTION OF FIGURES

FIG. 10 shows a cross-sectioned elevation view of a syringe cartridge of a manually-powered painless injection device of the present invention in an extended position, taken through line 10-10 of the syringe cartridge shown in FIG. 12.

FIG. 12 shows a plan view of the syringe cartridge of FIG. 10.

FIG. 13 shows a detailed cross-sectional elevation view of the syringe cartridge of FIG. 10.

FIG. 14 shows another detailed cross-sectional elevation view of the syringe cartridge of FIG. 10.

FIG. 15 shows a plan view of the syringe cartridge shown in FIG. 14.

FIG. 32 shows a separable base assembly having an adhesive flap for use in attaching the device of the present invention to the skin of a patient.

FIG. 33 shows a cross-sectioned elevation view of the separable base assembly of FIG. 32 through lines 33-33.

FIG. 34 shows a detailed cross-sectioned elevation view of the separable base assembly of FIG. 33.

FIG. 35 shows another detailed cross-sectioned elevation view of the separable base assembly of FIG. 33.

DETAILED DESCRIPTION OF INVENTION

Definitions

Figure 1:
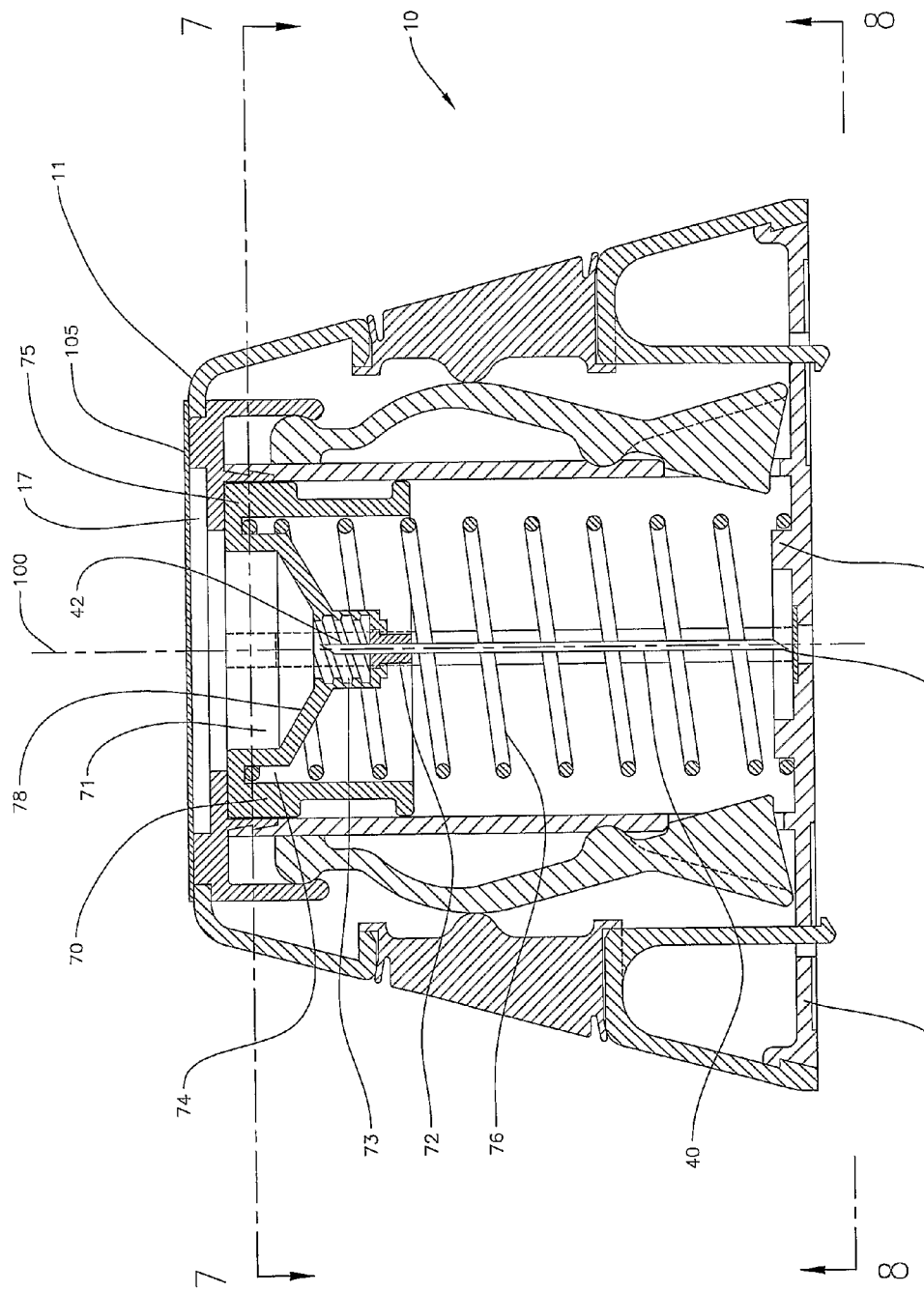
FIG. 1 shows a cross-sectioned elevation view of a housing of a manually-powered painless injection device of the present invention in an extracted position, taken through line 1-1 of the housing shown in FIG. 4.

As used herein, "patient" means a mammal, including a person, including a child or infant, or an animal, typically a mammal, on which the device is attached, and into whom the device injects an injectable liquid composition.

As used herein, unless specified otherwise, the phrase "manually powered" means that the power provided to the device of the present invention to at least insert the injection needle into the patient's body is provided manually by a person, including a medical technician (a nurse, doctor, or other person who can administer the injection) or a patient, by manipulating the injection device with the hands or fingers, or by manipulating an appropriate implement that interacts with the device.

As used herein, unless specified otherwise, the term "self-administering" describes the ability of the device of the present invention to be held or to hold itself in a position attached to the skin of a patient by a securement means, without requiring a medical technician, the patient, or other person, to hold the device, during the time that an injectable liquid composition contained within the device is injected into the patient through the injection needle.

As used herein, unless specified otherwise, the term "upward" means in a direction or oriented away from the patient's skin or the base of the device; the term "downward" means in a direction or oriented toward the patient's skin or the base of the device; the term "inward" means in a direction or oriented toward the centerline of the device, typically the needle; and the term "outward" means in a direction or oriented away from the centerline of the device.

The self-administering injection device of the present invention typically comprises a housing, an injection needle, a reservoir for containing an injectable liquid composition, such as a vaccine or a medicament, and a plurality of elements associated with and at least semi-permanently attached to the housing. The other associated elements can also include the various means of providing power or energy for the functional operations of the device, such as the insertion and retraction of the injection needle, and the pumping or injecting of vaccine to the injection needle. A self-contained, self-powered device embodiment will also have means for inserting the injection needle that is powered by an on-board element of the device. Typically, these associated elements are contained within the confines of the housing, although these elements can also partially confront or penetrate through the outer surface of the housing.

In the course of administering most injections of vaccines and other medicaments, the injection can be advantageously administered intramuscularly, that is, into the muscle. The injection is made with an injection needle that is configured for insertion through the outer layer of the patient's skin, and more typically into the muscle tissue of the patient. Typically, the depth of insertion is at least about 5 mm, and typically up to about 35 mm or more, more typically from about 10 mm to about 25 mm, and even more typically from about 15 mm to about 20 mm. For a young child or infant, the depth of insertion is typically from about 10 mm to about 25 mm, more typically from about 12 mm to about 15 mm. Alternatively, some injections can be administered intradermally, or into other internal organs or the general body cavity of the patient.

Painless injections can be achieved when the size or diameter of the injection needle is minimized, typically by using a needle of gauge size 28 or small (typically up to gauge size 33), and when the injectable liquid composition, such as a vaccine or other medicament, is injected at a volumetric flow rate significantly lower than that of a conventional injection made by hand, typically less than about 50 microliter per second ($\mu L/s$) and more typically about 1-4 $\mu L/s$. To achieve such low flow rates when administering a typical injection dose of between 0.5 ml to about 1.0 ml, an injection time of about 3 to 5 minutes may be needed. Typically, the human hand, using a conventional syringe, can not accurately or reproducibly control the flow rate within a range that ensures a painless injection. Furthermore, the desired slower injection rate of the medicament would require that the medical technician (or the patient) hold the conventional syringe carefully in place against the skin of the patient, and that the patient not move the limb or body part that is the site of the injection while the injection is being administered. The present invention overcomes these problems by providing a self-administering device that remains in position on the skin of the patient at the injection site, and administers the injection of the injectable liquid composition, without requiring a medical technician or patient to hold the injecting device in its place by hand, and without requiring that the patient remain still and not move while the injection is being administered. These problems are particularly troublesome when the patient is an infant or young child.

The self-administering device of the invention is intended to be attached semi-permanently to the skin of the patient before, during or after the injection. The device is typically configured to be attached to the upper arm or to the thigh area, providing access to the larger skeletal muscles (the deltoids and the quadriceps) for intramuscular injection. The attachment is preferably semi-permanent, whereby the device can be removed reasonably easily from the skin. The device is configured to attach to the body of the patient so that it does not move or migrate along the surface of the skin after attachment. In many situations, an adhesive attachment is sufficient. Alternative attachment means can include strapping, such as with a buckle strap or with a "hook and loop" attachment means commonly referred to as "Velcro", or cuffing, as with a sphygmomanometer cuff. In another alternative embodiment, a portion of the device, such as a bandage associated with the device or a portion of the base of the housing, can be configured to remain affixed to the patient's skin after the housing of the device has been removed.

A typical adhesive for securing the device directly to the skin is a pressure sensitive adhesive (PSA). The direct-attaching PSA and the base where the PSA is affixed are typically configured whereby the PSA adheres to the device more strongly than the PSA adheres to the skin. The PSA is typically permanently affixed to the device, such that no PSA will remain adhered to the skin of the patient when the device, or at least the housing portion of the device, is removed from the skin. The PSA is also selected for a secure though releasable affixment to the skin. These criteria ensure that the device, or at least the bandage or base portion of the device, can be securely affixed to the skin for the vaccination procedure, and can be safely and efficiently removed from the skin thereafter.

Typically, the manually-powered device having a skin-attaching PSA will also include a release member, such as a release paper or film, which overlies the adhesive on its skin-contacting side. After the release member is peeled from the PSA, the exposed adhesive layer can be placed against the patient's skin to attach the device thereto.

A main objective for initiating the development of the present injection was effecting a painless injection of injectable liquid compositions. While pain can be a relative experience, typically the painless device of the present invention will, after having been secured to the skin of the patient, effect the insertion of the injection needle and injection of the injectable liquid composition into the body without a sensation or feeling of pain, and more typically without any sensation or feeling whatsoever. In other words, the patient in most circumstances will have no sensation that the device has inserted a needle into the body, or that the injectable liquid composition is or has been injected into the body, except perhaps visually observing the device or touching the device with a hand, or feeling the attachment of the device to the outside of the skin.

Typically the manually-powered device is configured to complete the vaccination or injection of medicament into the patient utilizing a source of power or energy that is external to the device itself. The source of power can be provided by a person, such as a medical technician (a nurse, doctor, or other person who can administer the injection) or the patient, typically by manually (or bodily) manipulating the injection device with the hands or fingers, or by using an appropriate implement, as hereinafter described. The self-administering feature of the device and method of the invention enables injection of injectable liquid compositions without requiring medical personnel to hold the device against the skin of the patient during the time that the injectable liquid composition is in liquid communication with the needle, and is being pumped from the device into the patient. The use of the device that self-administers an injection allows medical personnel to perform other tasks while the injection proceeds. The device also allows the patient to have freedom of movement for the minutes of time that the injection proceeds. Typically, the source of power for arming the manually-powered device from its unarmed configuration comprises a manual power. This can be the use of the hands or fingers of a technician or an adult patient to manipulate the device or elements thereof with force. The manipulating force can also be applied using an implement, such as a key, push rod, or other inanimate object. The manually-applied kinetic force is stored by a power means within the device as potential energy, which can, upon subsequent activation, power one or more of the functions of the device. Typically, the external force used for the needle insertion function can also be used to store potential energy within the device, such as in a compressed spring or other biased resilient member. The external force can also be stored as electrical power or pneumatic power.

Typically, the self-contained device is intended to be self-powered, wherein the device comprises a power means to provide the energy necessary for one or more of the functions of the device, such as inserting the injection needle, pumping the medicament to the injection needle, and withdrawing the injection needle from the skin. The power means can include one or more such power means, each of which can employ one or more different forms of power. Typically, the power means include electrical power, supplied from a battery or electrical condenser. The power means can also include a pneumatic power means, such as a source of compressed gas or air. The power means can also include a fluidic power means, which includes both pneumatic and hydraulic power, such as a source of compressed air or gas, or hydraulic fluid. The power means can also include a mechanical power means, such as a compressed, stretched or torsioned spring, or a physical member that is biased into a strained or stressed position. The power means can also include a chemical power means, an electronic power means, such as an energized piezoelectric material, or an electrical power means such as an energized coil. The power means can also include an electro-chemical power means, where an electric charge or current can be converted into a chemical source of power, such as gas pressure from a gas generator. Non-limiting examples of self-powered, self-administering devices that can employ the improvements described herein are disclosed in US Patent Publication 20040116847, incorporated herein by reference.

The device can also be at least partially self-controlled, wherein at least one of the elements of the device can function automatically in response to the operation of another element. In some embodiments, all of the functioning elements of the device are actuating in response to the operation of one other element, or in response to some outside parameter, or automatically by time.

Typically, the device is manufactured and shipped to a use center, such as a clinic or hospital, with the needle insertion function in a first unarmed configuration. The unarmed configuration provides that the injection needle, which in its first position has its injection tip wholly within the housing, can not be intentionally or accidentally extended to a second position wherein the injection tip extends through the base of the device and outside of the device. In the unarmed configuration, there is typically no potential energy source, such as a compressed wire spring, available to the needle insertion means for spontaneous insertion of the needle. The unarmed condition can also be termed a fail-safe position, since, in this configuration, even a malfunction of the device will no allow the needle to extend from the housing. By contrast, if the needle insertion means is armed, then the device has potential energy stored on board, such as in a compressed, extended or torsioned spring, or other power means for insertion of the needle. If this armed device is activated, such as when an actuation button is depressed, the potential energy of the power means is released as kinetic energy that can move the needle insertion means from its first position to its second, extended position. If the device is shipped, stored, or handled in an armed configuration, there is a risk of an inadvertent, or even an intentional, activation of the needle insertion means. Consequently, the shipment and handling of the manually-powered device of the present invention in an unarmed configuration can avoid both an intentional and accidental needle sticks prior to its use in administering an injectable liquid composition. This improves the safety and security of the device during, storage, and pre-injection handling. In this configuration, at least the needle extension function (also called the insertion function when the needle tip extends into the skin of the patient) is unarmed.

Other functions, such as the pumping or injection means (for passing the injectable liquid composition through the injection needle) and the needle retraction means (to withdraw the needle from its second position in the body back toward its first position in the housing) can be configured for shipment and storage as either armed or unarmed. Preferably, the power means for the pumping means has an unarmed configuration, to avoid an accidental activation of the pumping of injectable liquid composition from the reservoir, which could prematurely empty the reservoir and render the device useless. Likewise, any needle retraction means is preferably shipped and stored in an unarmed configuration, to avoid the possibility of an unintentional or accidental activation, which in some embodiments may make the opposing needle insertion function inoperable, where the needle retraction is irreversible.

The power means can be used to provide energy to one or more of the elements of the device, such as insertion and retraction of the injection needle, or pumping of the medicament. Two or more power means can be used to provide energy for different elements, such as where the injection needle is moved from one position to another by a first power means, and an injectable liquid composition is pumped from a reservoir to the injection needle by a different, second power means.

The device can be at least partially self-controlled, wherein at least one of the elements of the device can initiate operation automatically in response to the operation of another element.

The typical device of the present invention has a housing comprising a base for placement against the skin of a patient for attachment of the device. The base can have a contoured surface that generally conforms to the shape of the body (typically, the arm or leg), to maintain the base surface in optimum confronting relationship with the skin. For example, the base of the device can have a slightly concave surface, which arches inwardly toward the interior of the housing.

The housing is typically made of a thermoplastic material that is light and inexpensive to manufacture, such as by molding, and yet is durable and resilient to gross deformation or breakage. A typical plastic material can include polyethylene, polypropylene, and polycarbonate. The housing can be designed with a shape that is both aesthetically pleasing and functional, for example, to allow insertion of the reservoir, to allow activation of one or more of the elements, such as the injection needle and liquid communication means, and other elements of the device. The housing can be made as a single part or as a plurality of parts configured to associate and secure together in both either static or moving relation to one another.

The housing also provides a visual enclosure for the injection needle that keeps the needle out of sight of the patient at all times during the injection procedure. This can reduce or eliminate the patient's apprehension or fear caused by the sight of a needle, thereby reducing the tendency of the patient's muscles to tighten and harden, which can make needle penetration more difficult and painful for the patient.

The housing also provides a physical enclosure for the injection needle that helps to avoid accidental needle stick, particularly after an injection, which could place a user at serious risk from fluid-borne pathogens. The device can be configured for use only once (unless completely disassembled and retrofitted), thereby minimizing the likelihood of reuse of a contaminated hypodermic needle. The device can also advantageously be configured wherein some parts or assemblies, such as the housing and it associated elements, can be reused.

The housing can also be configured to receive and secure the needle and optionally the reservoir of injectable liquid composition as a modular insert into the housing body. The housing can include two or more parts, at least one of which is movable relative to another, which can be configured into an open position wherein either the needle or the reservoir, or both, can be inserted into the body of the housing, or a closed position wherein the needle and/or reservoir are not accessible or retrievable from within the housing. The movable part can be a door or a panel that is movable to provide an access port into the housing. The door or panel can be hinged or removably affixed to the housing, or can be slidable away from the access port.

The injection needle of the device provides for liquid communication of the injectable liquid composition passing from the reservoir and through other liquid communication means of the device into the body tissue of the patient, from where the injectable liquid composition can dissipate into the surrounding tissue and throughout the body. The injection needle should be shaped and configured to provide painless insertion and painless injection of the injectable liquid composition. Generally an injection needle having a smooth circular outer surface and an outer diameter D of about 0.36 mm (28 gauge needle) and less can be inserted painlessly through the skin of a patient. For small children, infants and patients having more sensitive skin, an outer diameter D of about 0.30 mm (30 gauge needle) and less (31 gauge to 33 gauge), will typically ensure painless needle insertion.

Typically the injection needle is configured to be substantially linear or straight, from its tip toward the opposed inlet opening. The needle can be configured to be linear completely to its inlet end, or can be configured with a bent or curved portion near the inlet opening.

The needle size should be sufficiently large to allow passage of the required volume of liquid medicament into the body within a period of time that is suitable to avoid causing pain. For a typical medicament volume of about 0.5 ml to about 1.0 ml, a substantially painless to completely painless injection can be achieved over an injection period of from about 1 minute to about 10 minutes, more typically from about 3 minutes to about 5 minutes. The volumetric flow rate is at least about 0.05 microliter per second $\mu L/s$, and up to about 50 $\mu L/s$. Typically, the volumetric flow rate is about 0.5 $\mu L/s$ to about 20 $\mu L/s$, and more typically about 1 $\mu L/s$ to about 4 $\mu L/s$. The injection needle should be sufficiently durable and axially rigid to avoid bending or breaking when inserted into the skin and muscle. Typically, a needle having an outer diameter of from 0.20 mm (33 gauge), more typically of from 0.23 mm (32 gauge), to 0.36 mm (28 gauge), is sufficiently painless, durable, and liquid conductive.

It is also within the practice of the device and method of the present invention to inject medicament volumes of greater than about 1.0 ml, and to deliver the injection over time periods greater than 10 minutes.

Typically, the injection needle is pre-installed into the injection device during its manufacture, prior to its distribution to at the facility or site where the injection shall occur. Although the device can be configured for installation of the injection needle at the use facility, the small, fine size of the injection needle may make it difficult for a medical technician or patient to manipulate it into position within the device. Likewise, after a vaccination, the injection needle and the housing or assembly thereof into which the needle is secured can be disposed of in accordance with health and safety regulations and guidelines.

The liquid composition is typically contained within the cavity of the reservoir, and flows from the reservoir to the injection needle during injection. The reservoir is typically positioned within the housing although the structure of the reservoir can also form a portion of the outer surface of the housing. The reservoir can have a rigid structure having a fixed volume with a moveable member, such as a plunger that defines a variable volume cavity. The reservoir can also have a flexible structure where its volume can decrease as its content of medical technician or patient is removed there from. Typical materials for use in making the reservoir include natural and synthetic rubber, polyolefin, and other elastomeric plastics. The selection of the structure and material of construction of the reservoir will depend in part on the specific means of pumping the medicament from the reservoir to the injection needle. Selection of the material of the reservoir should also be chemically stable with the medical technician or patient. In another typical embodiment, the reservoir can be affixed to the injection needle as part of a liquid composition product, for assembly into the device. A reservoir will generally have a volume sufficient to contain about 0.1 ml to about 10 ml, typically about 0.1 ml to about 3 ml, of medicament. In a more typical embodiment, the reservoir would hold about 0.5 ml to about 1.0 ml of medicament.

The reservoir comprises an outlet port, typically comprising a penetrable membrane that can provide an air-tight and leak-proof seal over the outlet opening of the reservoir during manufacture, shipment and storage of the filled reservoir, and that can provide a self-sealing, leak-proof joint when pierced by the inlet end of the needle or a separate piercing conduit at the time of the injection. A typical reservoir membrane comprises natural or synthetic rubber or a thermoplastic material.

Alternatively, a wall of the reservoir can be adapted to allow penetration thereof by the piercing conduit, such as the inlet end of a needle.

A typical embodiment of a reservoir comprises a reservoir body having a cavity that has been pre-filled with the injectable liquid composition and sealed. The pre-filled reservoir can be assembled into the device during manufacture. In this case, the device is labeled to identify the particular injectable liquid composition that is contained therein.

More typically, pre-filled reservoir will be configured for installation or insertion into the housing of the injection device at the facility or site where the injection will occur. The technician would typically remove the reservoir from a storage area, such as a refrigerator, and insert it into position within the housing of the device. An identity label associated with the reservoir can be provided that is conveniently transferred to the patient's records.

Alternatively, a device comprising an empty reservoir can be filled by medical personnel with the appropriate quantity and type of medicament, prior to injection. Typically, this embodiment of the reservoir comprises a liquid composition flow valve that has a self-closing, self-sealing opening to the cavity of the reservoir. The liquid composition flow valve is typically an elastomeric or rubber material. The opening is typically a cylindrical member having a slit opening formed axially there through. The liquid composition flow value can be inserted into a bore formed in the sidewall of the reservoir that is slightly smaller in diameter than the flow valve. A hypodermic needle of a syringe can be inserted through the slit opening to inject a desired dose of the liquid composition into the cavity of the reservoir. When withdrawn, the slit opening closes and seals. When the device is used by medical personnel as supplied from a manufacturer with the reservoir securely inserted within the housing, the device can have a companion flow valve disposed in the surface of the housing, or otherwise accessible to the medial personnel. If the reservoir is configured so that a portion of the reservoir is integral with the housing, then a single flow valve can be used, with an inlet accessible to the medical technician and an outlet into the cavity of the reservoir. Alternatively, the device can be configured with a second liquid composition flow valve positioned in the housing, disposed adjacent to and aligned with the first flow valve disposed in the reservoir.

An important requirement of the liquid communication means is to ensure that the liquid composition can flow from the reservoir to the injection needle regardless of the specific orientation of the device. Typically, the attachment of the device to the skin of the patient can position the reservoir and the injection needle into a variety of relative spatial orientations that can sometimes require the liquid composition to flow upward against gravity, or that can position the outlet of the reservoir in an upward position, opposite the pool of liquid composition disposed in the reservoir.

Consequently, a preferred configuration of the reservoir and liquid communication means provides that the outlet of the reservoir is maintained in communication with the remaining liquid composition in the reservoir. A typical configuration comprises a collapsible reservoir comprising an outlet that maintains liquid communication with any residual liquid composition present in the reservoir. This reservoir has an upper flexible wall that can be conformed to the volume of the liquid remaining therein. The reservoir typically contains little or no air or gas when filled with the supply of liquid composition and during its displacement and injection operation. Thus, the reservoir collapses to become essentially empty, terminating delivery. In like manner, when a non-flexible material is used for a reservoir such as a conventional tube-with-plunger syringe, the displacement of the plunger empties the reservoir, which terminates delivery.

The housing can also comprise an outer support structure that confines and protects the reservoir from outside elements that might puncture it, and which can define the initial shape of the reservoir.

The reservoir can also be constructed of an elastomeric material that can be expanded in volume when filled with the liquid composition, and holds the liquid composition under pressure. After puncture by a piercing conduit, such as the inlet end of the injection needle or an intermediate member that is in liquid communication, such as via tube, with the injection needle, the expanded reservoir can contract to reduce the effective volume of the reservoir as liquid composition is pumped there from. One or more of the walls of the reservoir can be made of an elastomeric material, while other walls or surfaces are made of other elastic or inelastic rubber or plastic material.

The reservoir can also comprise an adaptable structure having a means of varying its effective volume, such as a piston-plunger construction or an accordion construction, as in a bellows. In the embodiments described herein, a self-contained reservoir can be replaced with a more conventional syringe and plunger for storing and injecting the liquid composition to the injection needle.

Non-limiting examples of a reservoir of the present invention are those described in U.S. Pat. No. 5,527,288 (element 10), U.S. Pat. No. 5,704,520 (element 12), and U.S. Pat. No. 5,858,001 (elements 16 and 17), all such publications incorporated herein by reference.

Figure 24:
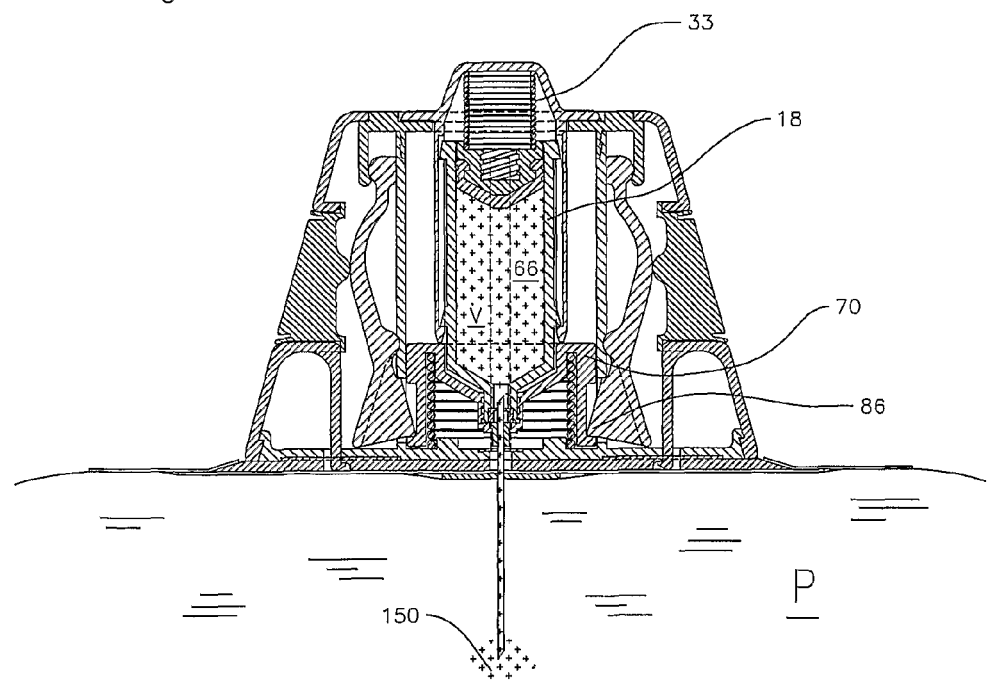
FIG. 24 shows the syringe cartridge in the inserted position within the housing, injecting the liquid composition.
Figure 25:
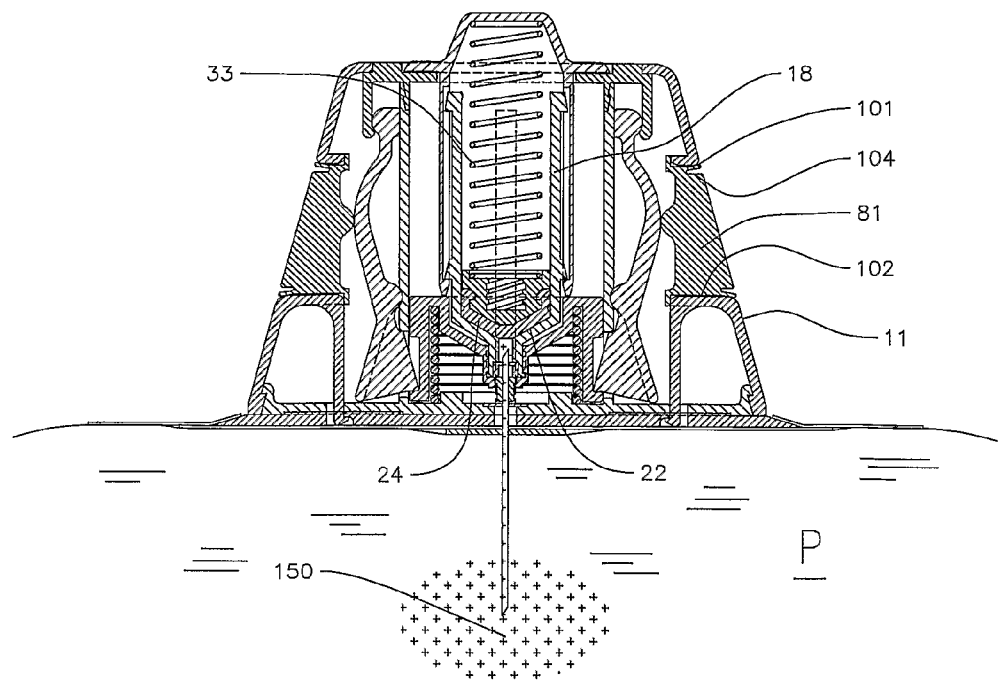
FIG. 25 shows the syringe cartridge in the inserted position within the housing, at the completion of the liquid composition injection.
Figure 29:
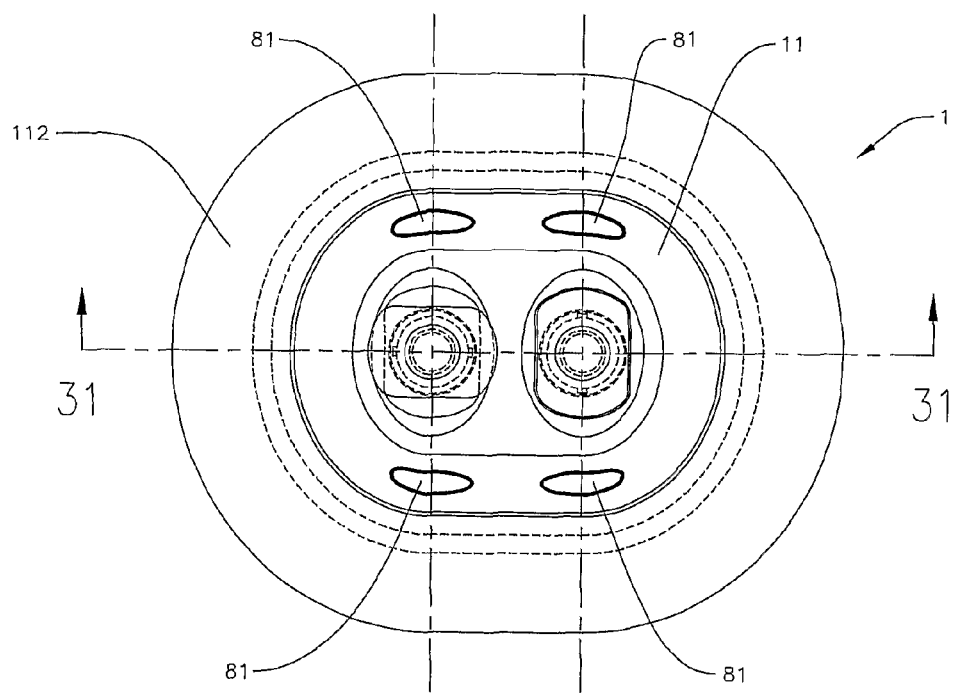
FIG. 29 shows a top plan view of another embodiment of the invention, of a device having a housing that can accommodate two syringe cartridges.
Figure 30:
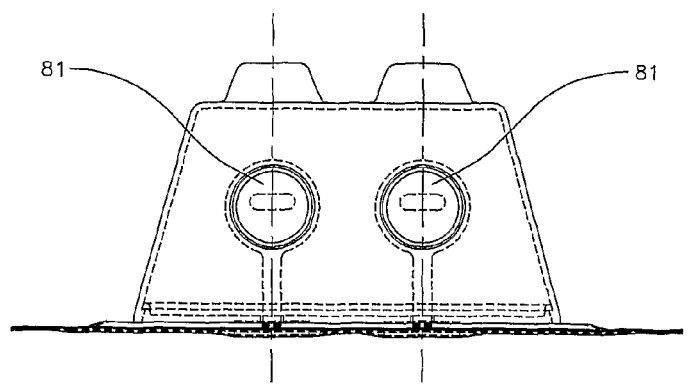
FIG. 30 shows an elevation view of the device of FIG. 29.
Figure 31:
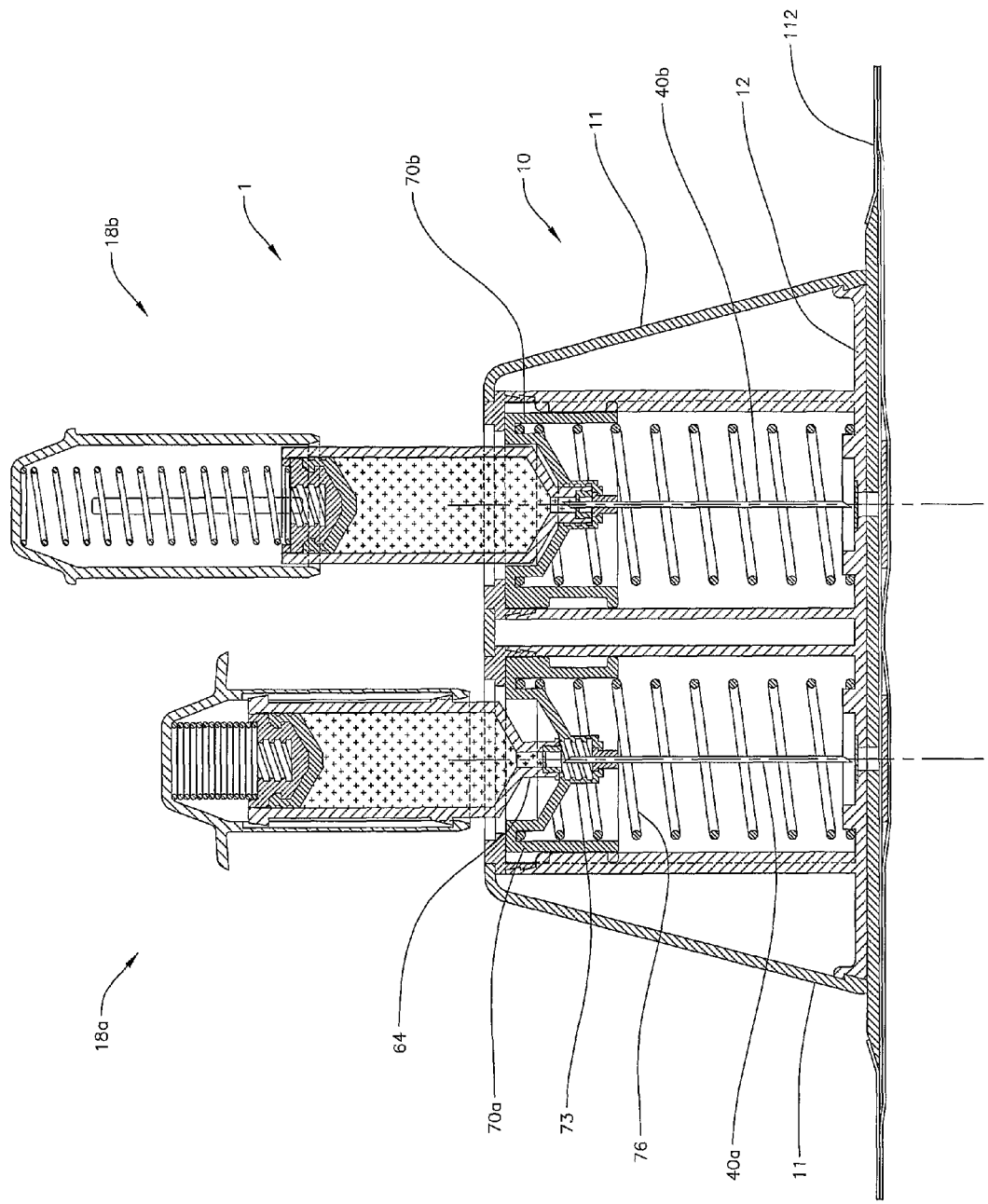
FIG. 31 shows a cross-sectioned elevation view of the dual-syringe device of FIG. 29 taken through line 31-31.

A first embodiment of the invention is shown in FIGS. 1-3, 3A, and 4-28. The device includes a housing, shown in FIGS. 1-3, 3A, and 4-9, and a cylindrical syringe cartridge shown in FIGS. 10-19. The use and operation of the device for manually self-administering a painless injection is illustrated in FIGS. 20-28. A device having a housing for retaining a plurality of cylindrical syringe cartridges is shown in FIGS. 29-31. FIGS. 32-25 show a separable base and means for attaching the device to a patient's skin.

FIGS. 1-8 show an assembled housing 10 in various views and aspects. FIG. 1 shows the housing 10 having an outer body 11, a needle carriage 70, a means for retaining a reservoir for an injectable liquid composition, and a base 12 for placement of the device against the skin of a patient. The carriage 70 is configured for movement along an axial centerline 100 in a direction perpendicular to the base 12. The cylindrical carriage has a cylindrical recess 71 having a tapered bottom 78, that opens to a connector portion 73 having internal female threads, which provide the at least a portion of the retaining means for the reservoir, described below. A needle 40 lies along the centerline 100 and is disposed through the axial center of a needle hub 72 that is secured to the connector 73. The inlet 42 end of the needle 40 extends within the connector portion 73 sufficiently below the opening in the tapered bottom 78 to prevent the sticking of a finger that may probe the recess. A retraction spring 76 is positioned about the centerline 100, having one end disposed within an annular groove 74 in the underside of carriage 70, and the other end disposed around an annular flange 94 projecting up from the base 12. The needle 40 extends downward from the lower end of the needle hub 72 toward the base 12. The needle is completely within the housing when the carriage 70 when in the first retracted position shown in FIG. 1.

Figure 2:
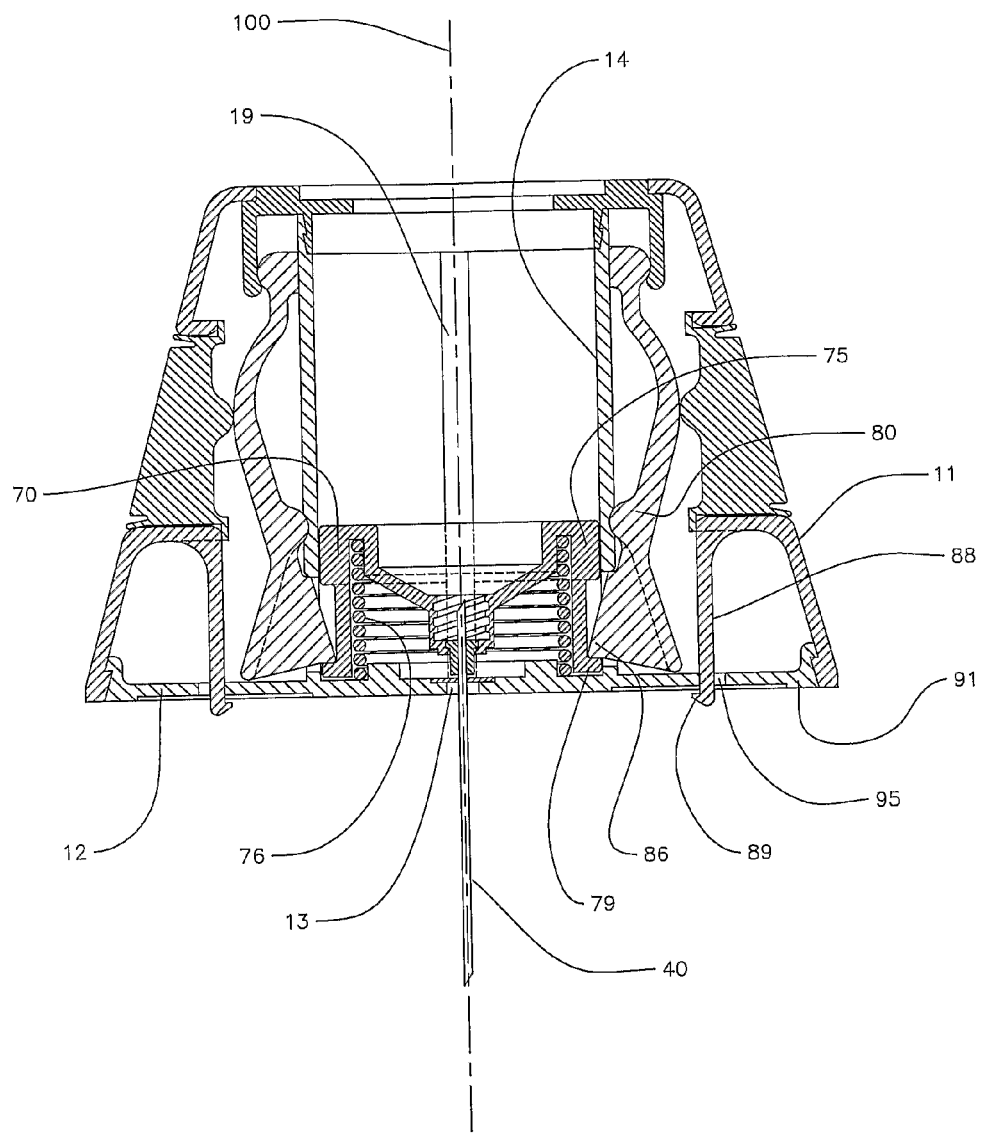
FIG. 2 shows the cross-sectioned elevation view of FIG. 1 of the housing in an inserted position.

In a second inserted position, shown in FIG. 2, the carriage 70 has moved axially toward a position proximate to the base 12 of the device, and the needle 40 extends downwardly and out through the opening 13 in the base. The guide wall 14 comprises an inwardly-projecting, axially-oriented elongated rib 19 that registers along its length with an axially-oriented peripheral groove 77 in the outer wall 75 of the carriage 70, shown in FIG. 3, to prevent the carriage 70 from rotating within the guide wall 14. A retainer heel 86 is biased inward from an opening in the cylindrical guide wall 14. As the carriage 70 passes down the guide wall 14, the heel 86 is temporarily biased outward, allowing the carriage to pass. The retraction spring 76 is compressed between the underside of the carriage 70 and the base 12. When the carriage arrives at the fully inserted position shown in FIG. 2, the lower end flange 79 of the carriage has cleared past the heel 86, which returns to its inwardly-biased position, where it can secure the carriage 70 and the needle 40 in the inserted position, and secures the retraction spring 76 in a compressed state. The heel 86 is part of a release arm 80, described herein after.

Figure 4:
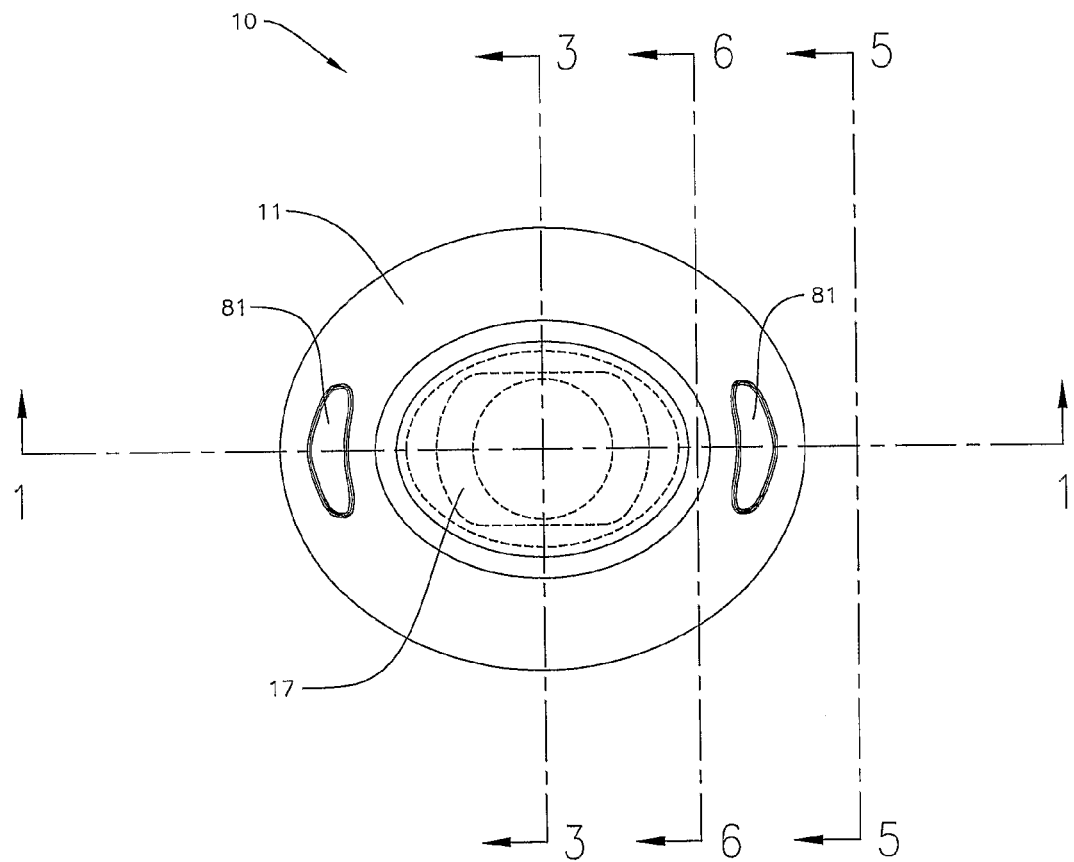
FIG. 4 shows a top plan view of the housing of the manually-powered painless injection device.
Figure 7:
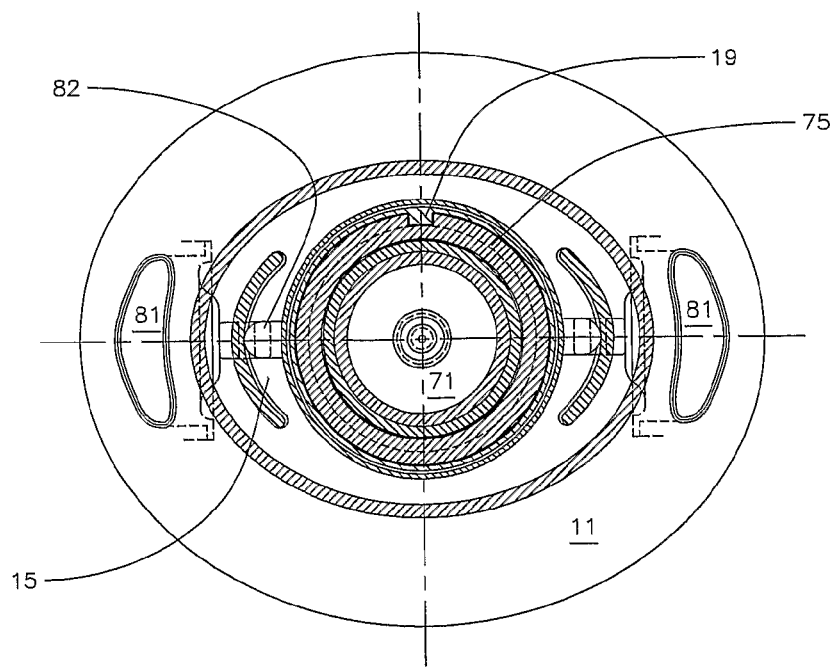
FIG. 7 shows a cross-sectioned plan view of the housing of FIG. 1, taken through line 7-7.
Figure 8:
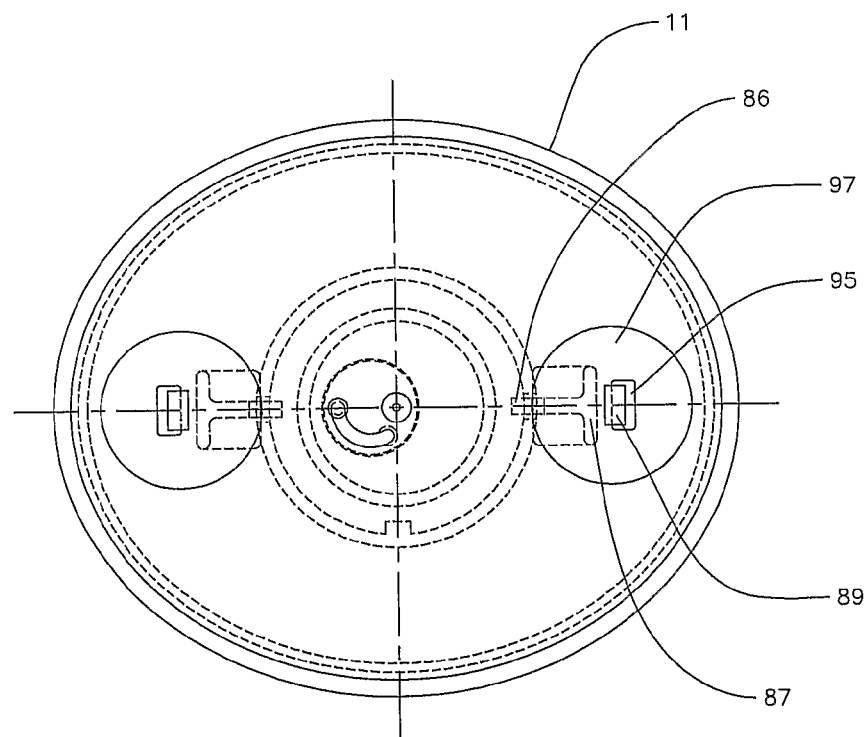
FIG. 8 shows a cross-sectioned plan view of the housing of FIG. 1, taken through line 8-8.
Figure 9:
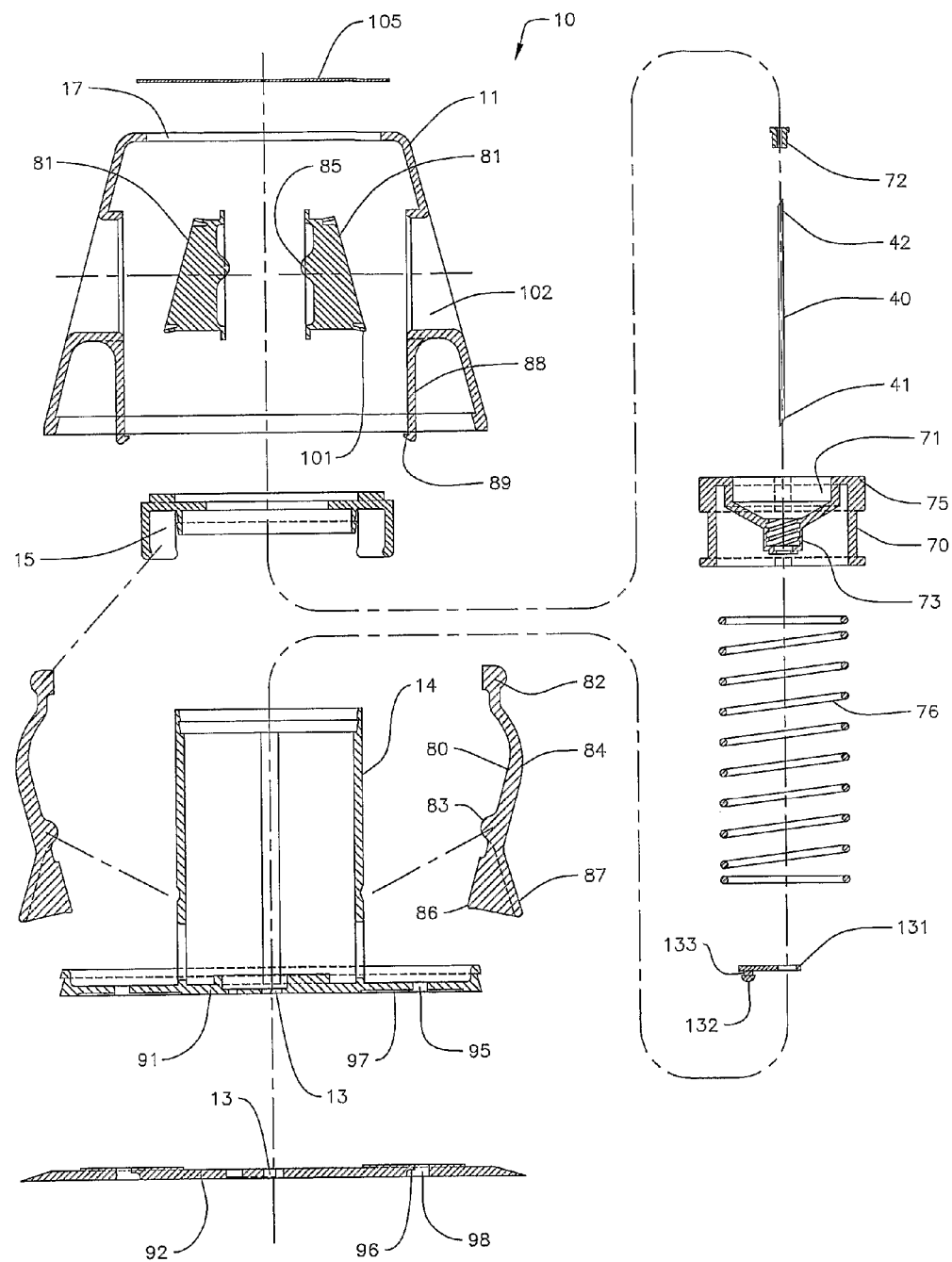
FIG. 9 shows an exploded cross-sectioned elevation view of the elements of the housing of FIG. 1.

FIG. 4 shows a plan view of the housing 10 in its first retracted position, with selected cross-sectional views taken as FIGS. 1, 3, 5, and 6 to illustrate certain elements of the housing. FIGS. 7 and 8 are sectional views of the housing in FIG. 1. An exploded view of the elements of the housing 10 is shown in FIG. 9.

Figure 11:
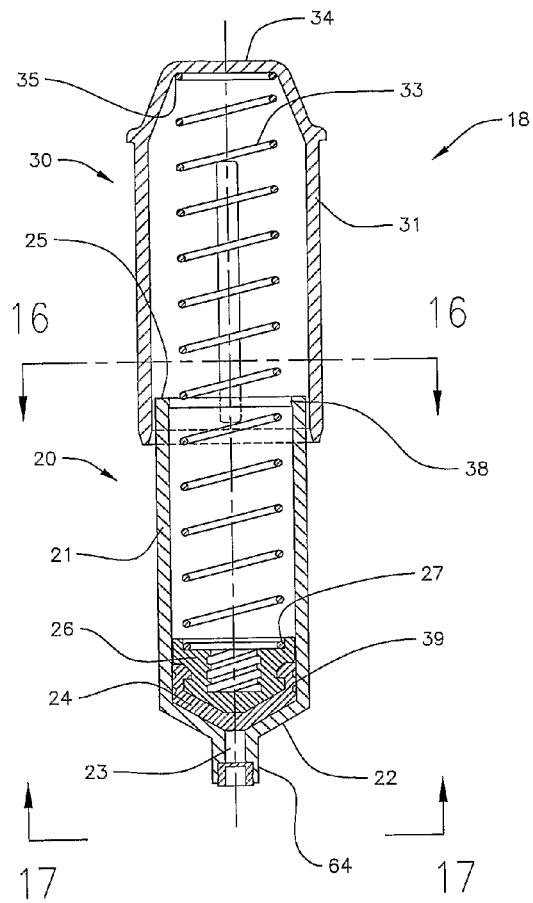
FIG. 11 shows a cross-sectioned elevation view of the syringe cartridge in an extended position, taken through line 11-11 of FIG. 12.
Figure 17:
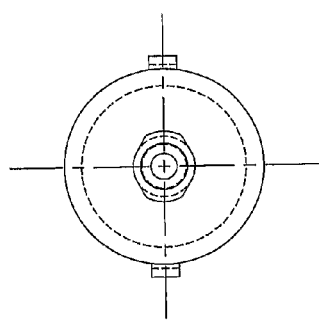
FIG. 17 shows a bottom plan view of the syringe cartridge of FIG. 11.
Figure 16:
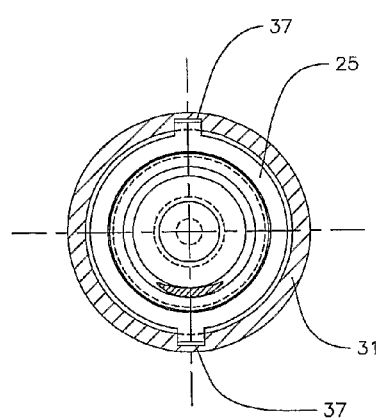
FIG. 16 shows a cross-sectioned plan view of the syringe cartridge of FIG. 11.
Figure 18:
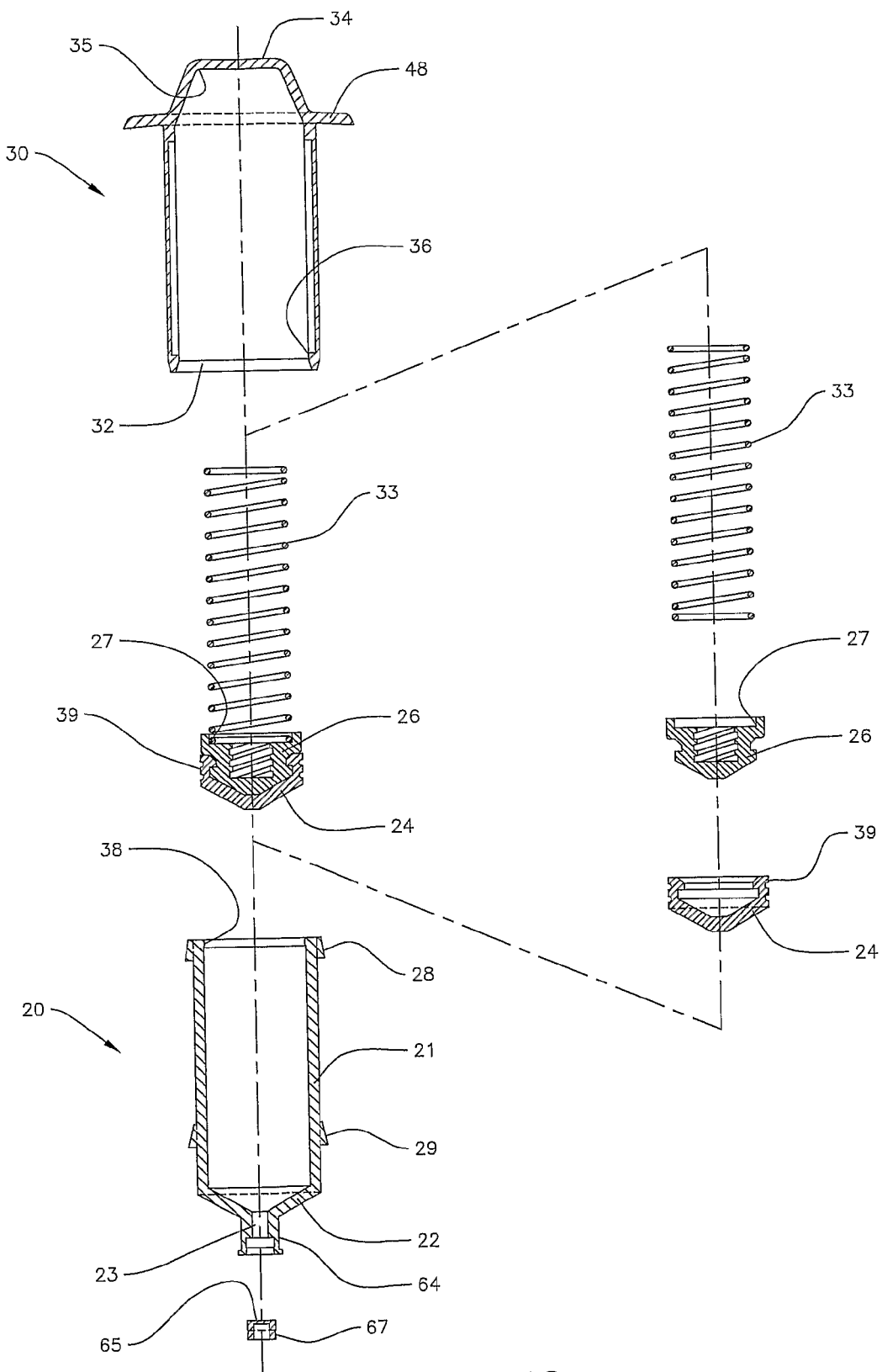
FIG. 18 shows an exploded cross-sectioned elevation view of the elements of the syringe cartridge of FIG. 10.

FIGS. 10 and 11 are sectional views of the syringe cartridge 18 taken through perpendicular section lines 10-10 and 11-11 of FIG. 12. FIGS. 13-17 provide additional detailed views of the syringe cartridge 18 shown in FIGS. 10 and 11. FIG. 18 shows an exploded view of the elements of the syringe cartridge 18.

The syringe cartridge 18 shown in FIGS. 10 and 11 comprises a syringe assembly 20 and a telescoping pressurizing assembly 30, configured as a reservoir having liquid cavity 66 for the injectable liquid composition. The syringe cartridge 18 is configured to be associated with and retained within the housing 10 of the device. In the illustrated embodiment, the cylindrical recess 71 of the needle carriage 70 provides the means for retaining the reservoir of injectable liquid composition, embodied by the syringe cartridge 18. The syringe assembly 20 comprises a syringe body comprising a cylindrical wall 21 that has an open upper end 25 and a tapering base 22 that has, at the lower end, an externally-threaded syringe hub 64 having an aperture 23. A cylindrical plunger 24 can be inserted through the opening in the upper end 25 for engagement with the inner surface of the wall 21. The space between the plunger 24 and the syringe body in FIG. 10 defines the reservoir cavity 66. The respective threads of the syringe hub 64 of the syringe cartridge and of connector portion 73 of the needle carriage cooperate and engage when the syringe cartridge is placed into the needle carriage and rotated, which secures or locks the syringe cartridge into its retained position within the needle carriage. The cooperating threads also provide liquid communication between the injection needle and the reservoir of the syringe cartridge, as the inlet 41 end of the needle advances and penetrates a membrane 65 of the membrane plug 67 disposed in the opening of the syringe hub 64 (see FIG. 14).

The plunger 24 is typically a flexible, resilient rubber material that can form an effective liquid seal about its periphery with the sidewall 21 of the syringe. The plunger 24 is secured around a rigid plunger plug 26 to maintain its cylindrical shape. As can be seen in greater detail in called-out FIG. 13, the inner surface of the syringe wall 21 has, at its upper end, a slight inwardly-extending rim 38 that can engage the upper end of the outer wall 43 of the plunger 24, which can prevent the plunger 24 from incidentally withdrawing from and falling out of the upper opening of the syringe wall 21. Nevertheless, the plunger wall 43 is sufficiently flexible to be inserted into or extracted out of the syringe opening by force.

The threaded bore in the plunger plug 26 is provided for attachment of a stem (not shown) having a mating thread so that the plug 26 and the plunger 24 secured thereto can be manipulated into and out of the syringe opening, and along the length of the syringe.

The telescoping pressurizing assembly 30 comprises a cylindrical body 31 that is closed at an upper end 34 and has an opening 32 at the opposed lower end. The lower edge of the cylindrical body 31 has a pair of opposed mechanical engaging means shown as inwardly-extending ribs 36 that can engage an outwardly-extending rim 28 disposed on the upper end 25 of the syringe wall 21, to secure the pressurizing assembly 30 to the upper end 25 of the syringe assembly 20 in a first extended position, as shown in FIGS. 10 and 13. A pressurizing spring 33 is restrained within the body 31 between an annular groove 35 at the closed end 34, and an annular groove 27 in the plunger plug 26. When the pressurizing assembly 30 is in the extended position shown in FIG. 10, the pressurizing spring 33 is typically under minimal compression. FIG. 11 shows the same syringe cartridge as in FIG. 10, but with the plunger 24 and the pressurizing spring 33 extended to the bottom of the syringe body 21. In this configuration, a medical technician can fill the syringe assembly. The upper pressurizing assembly 30 and the membrane plug 67 are first removed. Then, using a threaded stem (not shown), the plunger can be pulled upward to draw injectable liquid composition through the aperture 23. The membrane plug 67 and the upper assembly 30 then can be reinstalled.

Figure 19:
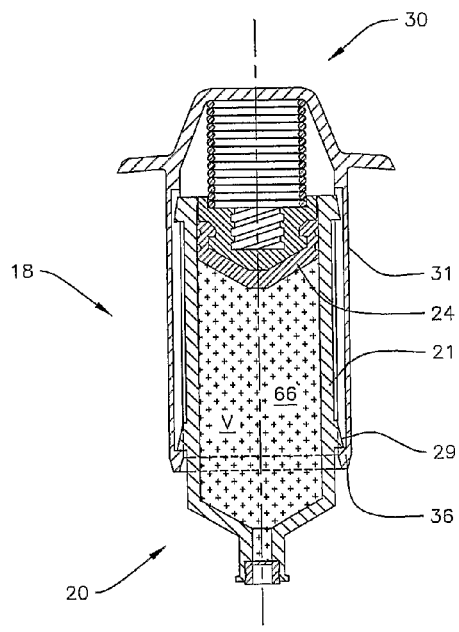
FIG. 19 shows a cross-sectioned elevation view of the syringe cartridge of FIG. 10 containing an injectable liquid composition in a pressurized position.

The wall 31 of the pressurizing assembly 30 is configure to telescope axially over the outside of the syringe wall 21 to a second pressurizing position (shown in FIG. 19), where the ribs 36 can engage a second set of outwardly-extending rims 29 disposed near the lower end of the syringe wall 21, also shown in FIG. 10. This causes the closed upper end 34 of the pressurizing body 31 to compress fully the pressurizing spring 33 against the plunger plug 26, which causes the plunger 24 to move to the bottom 22 of the syringe 21 when no liquid is contained in the cavity 66 of the syringe. The engagement of the ribs 36 with the lower rims 29 retains cylindrical body 31 in the fully pressurized configuration. When the cavity 66 of syringe 21 contains a volume of injectable liquid composition, such as vaccine V as shown in FIG. 19 the manual depressing of the syringe cartridge causes the compression of the pressurizing spring 33. The engagement of ribs 36 with rims 29 restrains the compressed pressurizing spring 33, and retains the potential energy within the compressed spring 33 as a means for injecting the liquid composition from the cavity. The manually-powered, compressed spring 33 exerts a downward force upon the plunger 24, which exerts pressure upon the liquid composition in the cavity 66. When the cavity 66 is put into liquid communication with the needle, the pressurized liquid vaccine can flow out of the cavity 66 under pressure. The pressurizing spring 33 is configured and designed to maintain a relatively constant force, resulting in a relatively constant pressure and liquid composition flow rate through the needle throughout the injection process.

The device 1 of the present invention comprises a separable base 92, from which the housing 10 can be removed at any time, particularly and advantageously after completion of the injection. The separable base 92 is typically configured for separable securement to the base 12 of the housing by a base securement means, and typically provides the skin-contacting surface of the device 1. A base separating means provides selective separation of the separable base 92 from the device.

Figure 27:
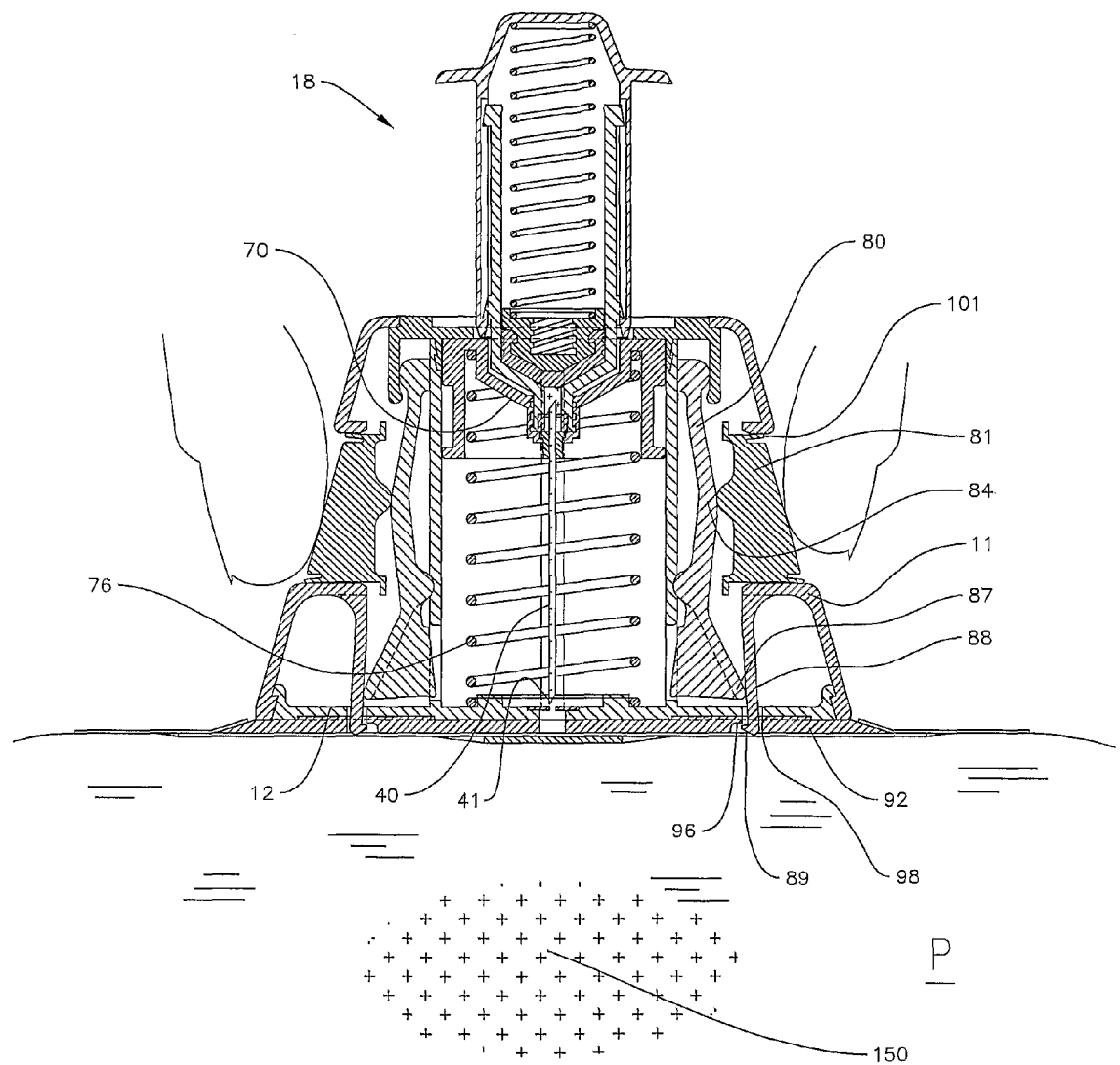
FIG. 27 shows the syringe cartridge and housing of FIG. 26, with the needle retracted.
Figure 28:
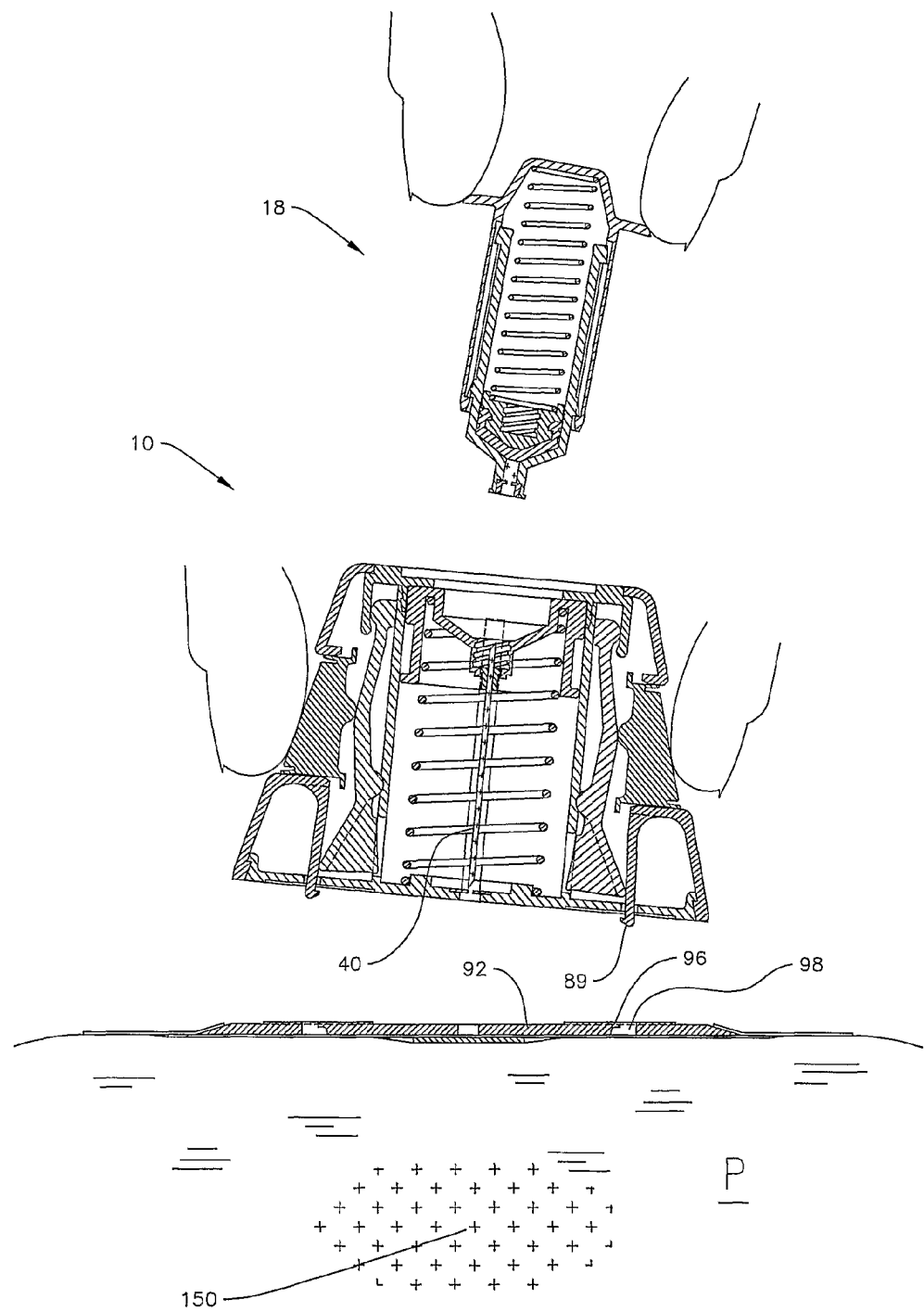
FIG. 28 shows the housing and the syringe cartridge of FIG. 27 being removed from the separable base that remains attached to the patient.

FIGS. 2, 27 and 28 illustrate an embodiment of a separable base 92, as embodied in a separable attachment assembly 93 that removably associates with the base 12 of the housing 10.

The base securement means can comprise a mechanical engagement, such as a catch 89 formed on a distal end of a release finger 88 that depends downward from a portion of the housing body 11. The distal end of the finger 88 extends through an opening 95 in an inner base member 91 shown in FIG. 2. The finger 88 further extends through an opening 98 in the removable base 92 when the removable base 92 is positioned against the base 12 of the housing. The finger 88 is configured to bias the catch 89 toward and into engagement with a latch 96 formed in the separable base 92, shown in FIG. 27. The separable base 92 remains affixed to the housing of the device provided that the catch 89 remains engaged with the latch 96.

The base separating means for separating the separable base 92 from the permanent housing base 12 can comprise a mechanically-biased member associated with the housing 10 that is configured for manipulation that forces to disengage the base securement means, specifically in the illustrated embodiment by moving the catch 89 out of engagement with the latch 96. In FIG. 27, after the needle 40 and carriage 70 have been retracted, the person can depress the release button 81 even further, thereby causing a toe 87 on a release arm 80 to pivot into engagement with the release finger 88, and to bias the catch 89 out of engagement with latch 96. With the catch 89 disengaged from latch 96, and with the needle 40 fully retracted, the housing can be safely and easily separated from the separable base 92 for post-injection inspection, and for disposal.

The separable base further comprises a means for attachment to the skin of the patient. Typically, the means for attachment comprises an adhesive means adhered to the skin-contacting surface of the separable base.

While the figures and associated description describe the separation of the separable base from the housing while the device is attached to the skin of a patient, it can be understood that the separable base can also be removed from the housing while the device is free from attachment to the body.

Figure 20:
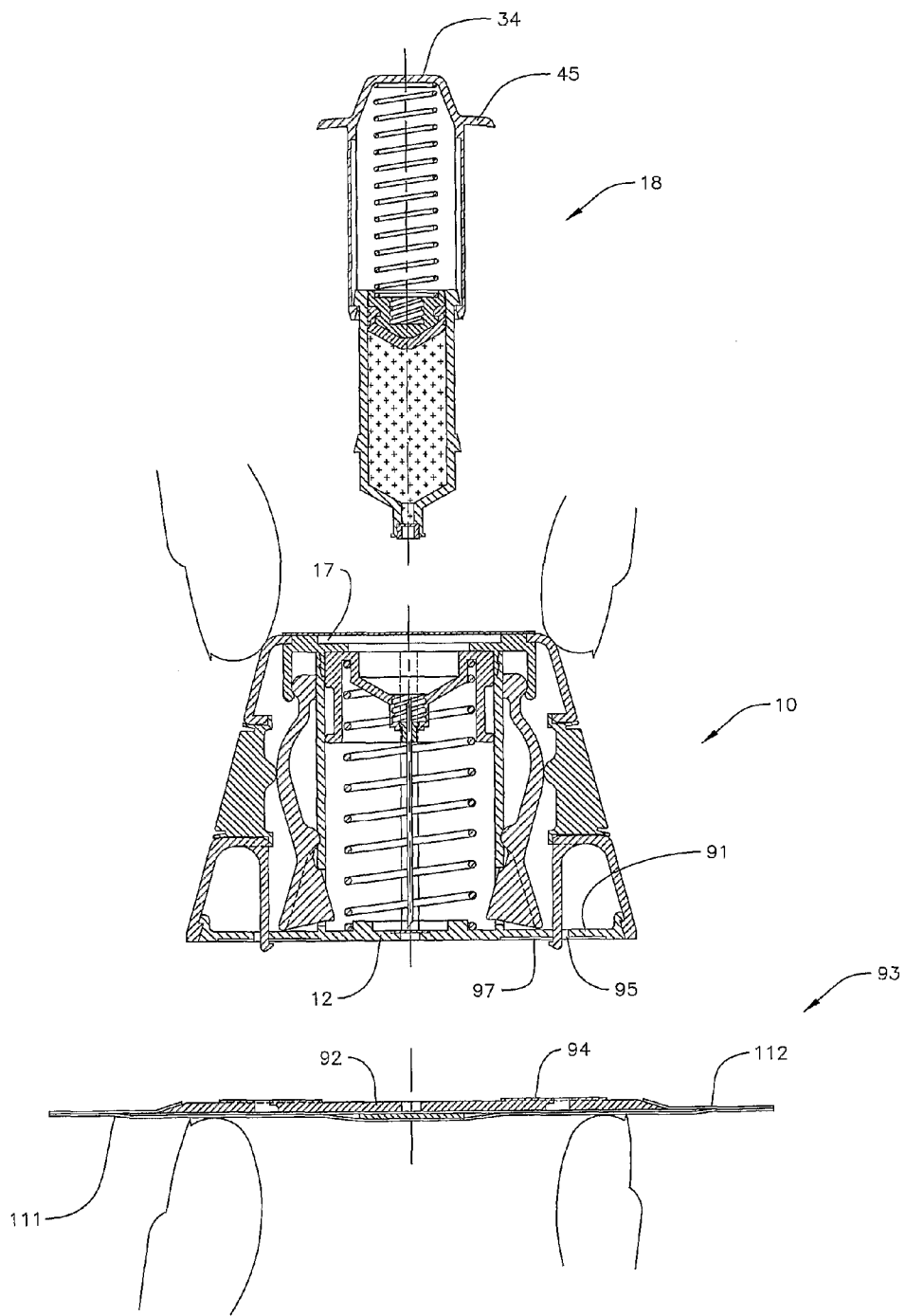
FIG. 20 shows a cross-sectioned elevation view of the housing and a separable base assembly prior to its attachment to the housing, and of a syringe cartridge prior to its installation into the housing.

In a method of using the device of the invention, a device 1 is provided as shown in FIG. 20 comprising a housing 10 having a separable attachment assembly 93 comprising a separable base assembly 92, and a syringe cartridge 18. The three members are shown separated to illustrate, that prior to use as an assembled product, the components can be separated and visually inspected.

The separable attachment assembly 93 can be attached manually to the base 12 of the housing 10 as previously described. Prior to attachment of the device to a person, a release paper 111 that covers the separable base 92 and adhesive flaps 112, is peeled away and disposed of.

Figure 21:
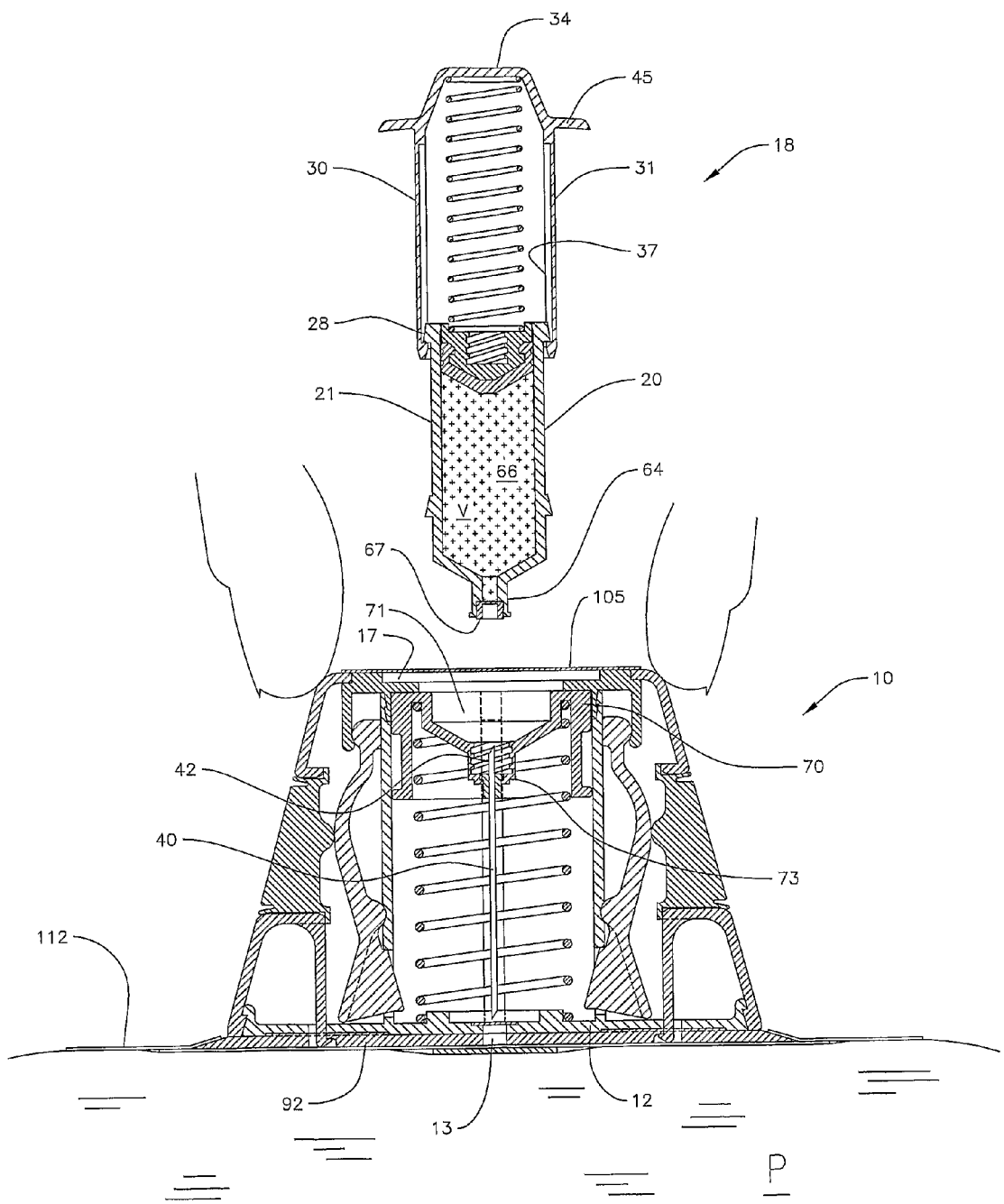
FIG. 21 shows the housing and syringe cartridge of FIG. 20, with the housing being affixed to a patient's skin.

As shown in FIG. 21, the separable attachment assembly 93 of the housing 10 can be attached to an area of the patient's skin on the upper arm or leg of the patient P, designated as the injection site, secured by the adhesive on the underside of the adhesive flap 112 that extends outward from the periphery of the separable base 92.

Figure 22:
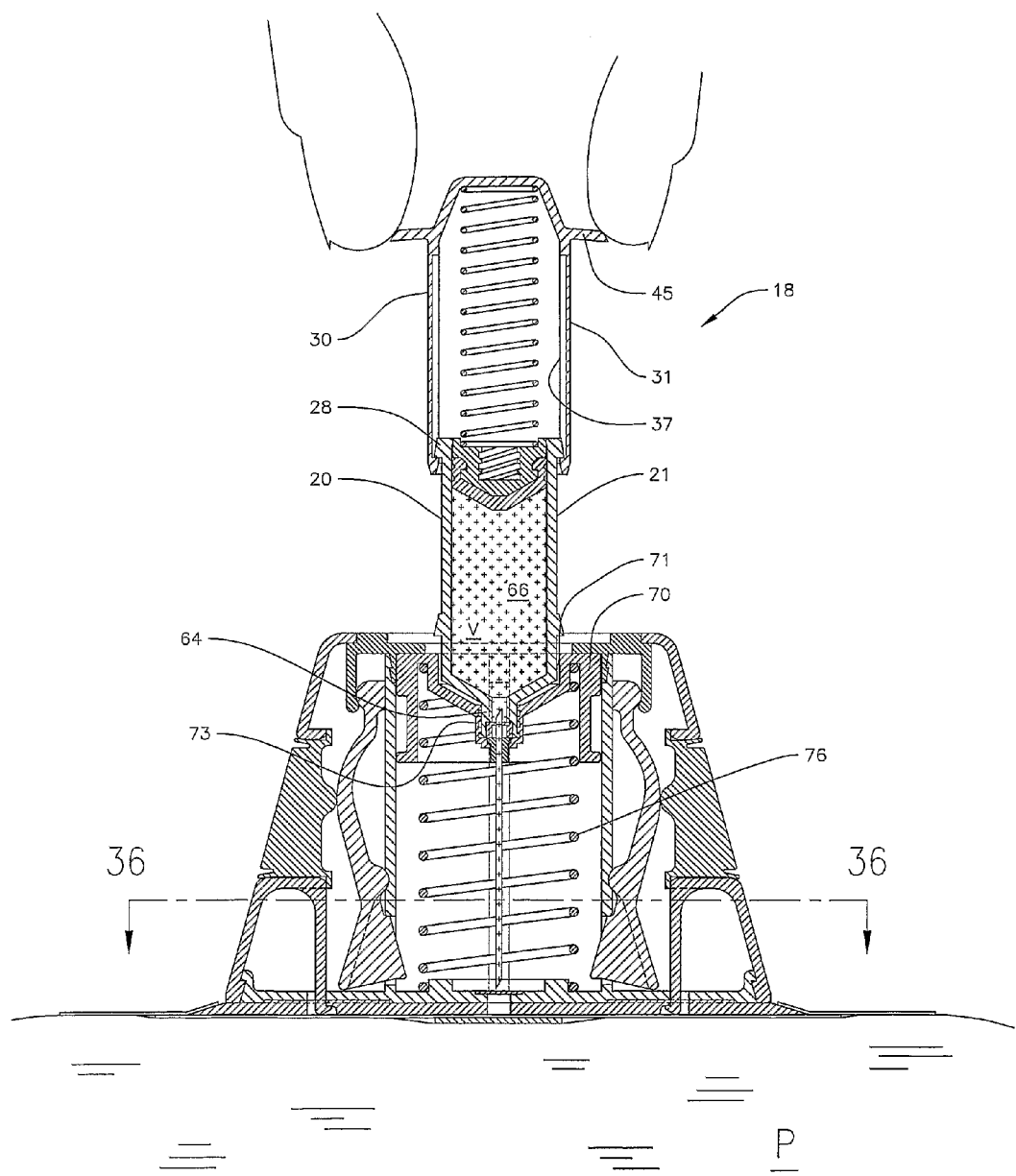
FIG. 22 shows the syringe cartridge being installed into the housing of FIG. 21.

After attachment of the device to the skin, a seal 105 is removed that covers the opening to the carriage recess 71 to protect the inlet end 41 of the needle 40 from contamination, as shown in FIGS. 21 and 22. The syringe cartridge 18 is then inserted into the recess 71 of the carriage 70. The threaded syringe hub 64 engages the threaded connector 73, so that manual axial rotation of the syringe cartridge 18 mates the respective threads and secures the syringe cartridge 18 to the carriage 70. As that occurs, a membrane 65 disposed in the opening of the syringe hub 64 (see FIG. 14), is penetrated by the inlet 41 end of the needle, which establishes liquid communication with the syringe cavity 66. A pair of tabs 45 extending out from the top of the pressurizing body 31 provides a grip for manually rotating the syringe cartridge 18 into the carriage 70. Relative axial rotation between the syringe assembly 20 and the pressurizing assembly 30 is prevented by disposing the outwardly-extending rims 28 of the syringe wall 21 into longitudinal grooves 37 formed in the inner surface of the pressurizing body 31.

In an alternative method, the syringe cartridge 18 can be provided in its pressurized configuration, as shown in FIG. 19, just after the technician has compressed the telescoping pressurizing assembly 30 down onto the syringe assembly 20, and just prior to insertion of the cartridge 18 into the carriage 70, shown in FIG. 22. When the technician inserts the pressurized cartridge 18 into the recess 17 of the carriage 70, and rotates or twists the cartridge 18 to establish liquid communication between the reservoir cavity 66 and the needle 40, liquid composition may begin to flow from the syringe cavity and into and through the needle 40.

The device can also be configured to prevent rotation and removal of the modular syringe from its position in fluid communication with the needle, once the carriage 70 has been moved to and secured in the injection position. The tabs 45 extending from the closed end 34 of the pressurizing assembly 30 nest within the oblong recess 17 in the top of the housing 10 to inhibit finger access to the assembly, and to prevent manual rotation and removal of the syringe cartridge 18 in the injection position. This prevents an unwanted exposure of a needle that is penetrating the skin from being open at its inlet 42 end to the atmosphere.

Figure 23:
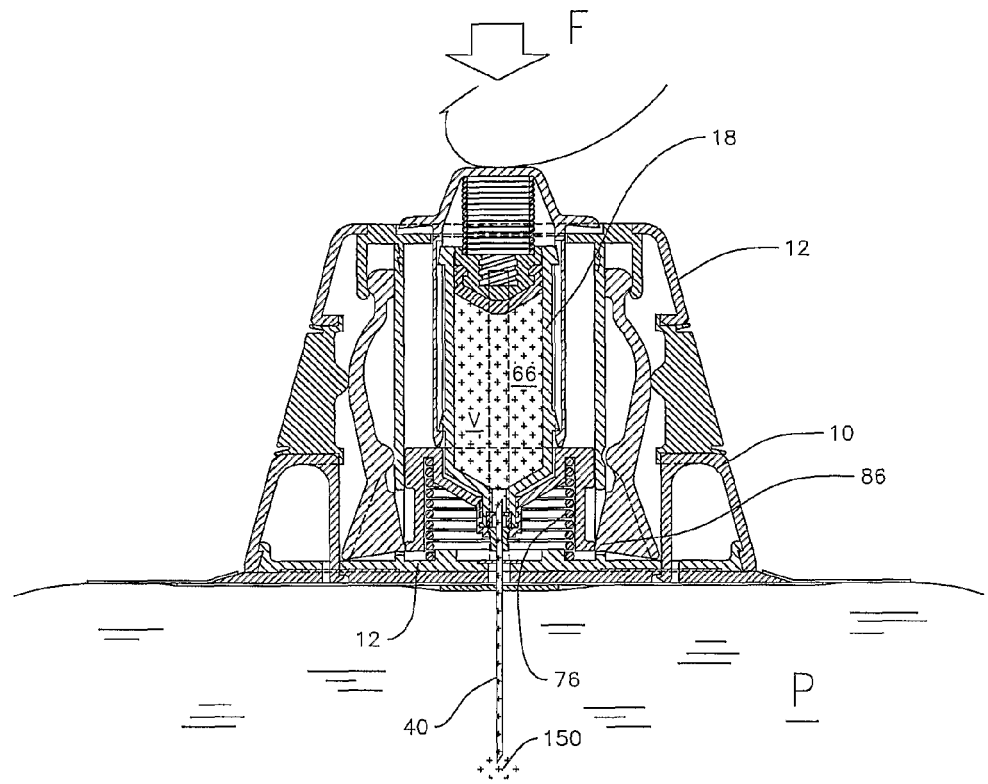
FIG. 23 shows the syringe cartridge being force into an inserted position within the housing.

As shown in FIG. 23, the needle 40 is then inserted into the patient by manual force downward on the syringe cartridge 18 to move it into the housing 10 and toward the base 12, thereby inserting the injection needle 40 into the body and initiating the injection. The pressing downward of the syringe cartridge 18 has also compressed the retraction spring 76. Fully manually pressing the syringe cartridge 18 downward causes the carriage 70 to be retained in a second position associated with the second injection position of the injection needle. A needle insertion securement, such as the retainer heel 86 shown in FIG. 24, is configured to retain the needle carriage, and the injection needle, in the second, inserted position while the liquid composition is injected. Under the relatively constant force of the pressurizing spring 33, the vaccine V is slowly though constantly expressed out of the syringe cavity 66 and into the targeted body tissue 150. The size of the needle and the force factor of the pressurizing spring 33 can be configured and designed to cause the liquid composition to flow under pressure through the needle within a target volumetric flow rate, to complete the injection within a prescribed period of time.

At the end of the injection term, shown in FIG. 25, the plunger 24 has moved under the force of spring 33 to the bottom 22 of the syringe, and has collapsed the reservoir cavity 66 and driven substantially all of the vaccine out of the syringe cartridge 18.

An alternative method of inserting the needle 40 can employ the syringe cartridge 18 itself as an "implement or plunger" for depressing the needle cartridge to its inserted position, without having the needle inlet 41 penetrate the membrane 65 to the syringe cavity and placing the needle into liquid communication with the cavity. The syringe hub 64 of syringe cartridge 18 can be rested against the bottom of the carriage 70, as shown by the left-side syringe in FIG. 31, and pressed downward with having engaged the threads, or having only partially engaged the threads, of needle hub 72 and connector 73. Alternatively, the syringe hub 64 and the connector 73 can be configured to provide a first position wherein the threads partial engage without establishing liquid communication between the needle and the cavity (that is, without rupturing the membrane 65), and a second position wherein the threads further engage and establish liquid communication by penetration of the membrane by the inlet end of the needle.

Figure 26:
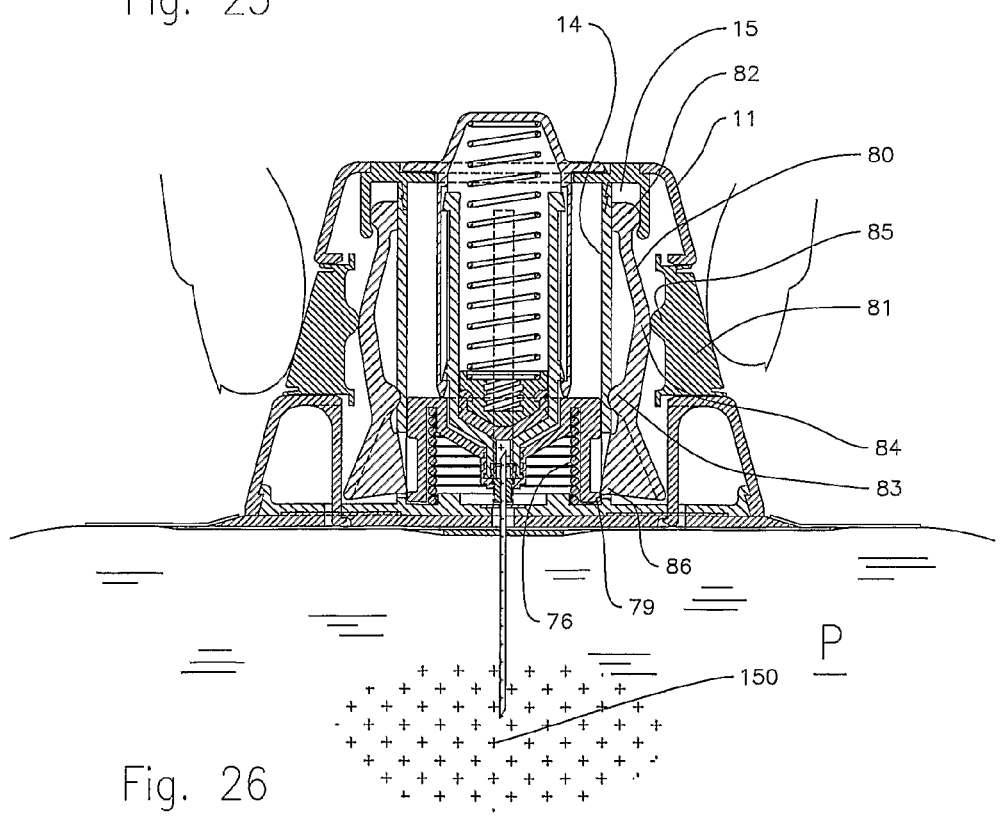
FIG. 26 shows the syringe cartridge in the inserted position within the housing of FIG. 25, being manipulated to retract the needle.

Once the injection has been completed, or at any time during the vaccination, the needle can be retracted from its second or inserted position by activating a needle retraction means. The needle retraction means can comprise a disengagement means that is configured to disengage the needle insertion securement, and a power means configured to bias the needle, and the needle carriage, to respective third positions where the injection end of the needle is disposed within the housing. In the illustrated embodiment of FIG. 26, the disengagement means comprises one or more release arms 80 and one or more release buttons 81. The release arm 80 comprises an upper end 82 shown as a ball having an inward flat surface that is secured within a socket 15 formed in the main body 11. The release arm 80 also comprises a pivot 83 that resides in a detent in the outside of the guide wall 14, and a resilient, flexible elbow portion 84 intermediate the ball end 82 and the pivot 83. A lateral bar 85 on the inside of the release button 81 is disposed proximate the elbow 84. In response to an inwardly-directed force on the button 81 that moves the button inward, as shown in FIG. 26, bar 85 causes the release arm 80 to flex inwardly at the elbow 84, causing heel 86 to pivot outwardly and out of engagement with the carriage lower flange 79. As shown in FIG. 27, the power means comprises a compressed retraction spring 76 that had been manually disposed into a compressed configuration when the needle was manually inserted, and biases the needle toward a third position. With the needle carriage 70 unsecured by the needle insertion securement, retainer heel 86, the compressed retraction spring 76 can drive the carriage 70 upward from the base 12, and retract the needle tip 41 completely out of the body of the patient P and into the third position where the needle tip is within the housing 10.

The needle insertion securement and the disengagement means can function through or comprise the same element of the device (like the release arm 80 which functions to both secure the carriage and to disengage the securement), or can employ distinct elements.

After retraction of the needle 40, the syringe cartridge 18 can be grasped and removed by oppositely rotating the cartridge to disengage the threaded connection of the cartridge with the carriage. The cartridge assembly 18 can be inspected to confirm that all the liquid composition from the syringe cavity 66 had been injected, and then is disposed. If for any reason a significant amount of the liquid composition remained in the syringe, the syringe cartridge 18 can be reinserted into the carriage 70 and again rotated into liquid communication with the inlet of the needle 40, and the carriage and needle reinserted into the patient to complete the injection.

Figure 5:
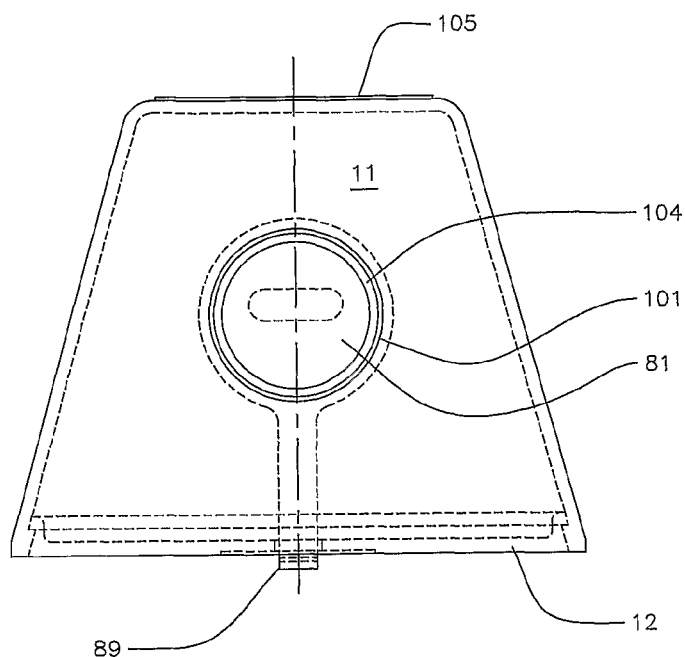
FIG. 5 shows a cross-sectioned elevation view of the housing of FIG. 4, taken through line 5-5.
Figure 6:
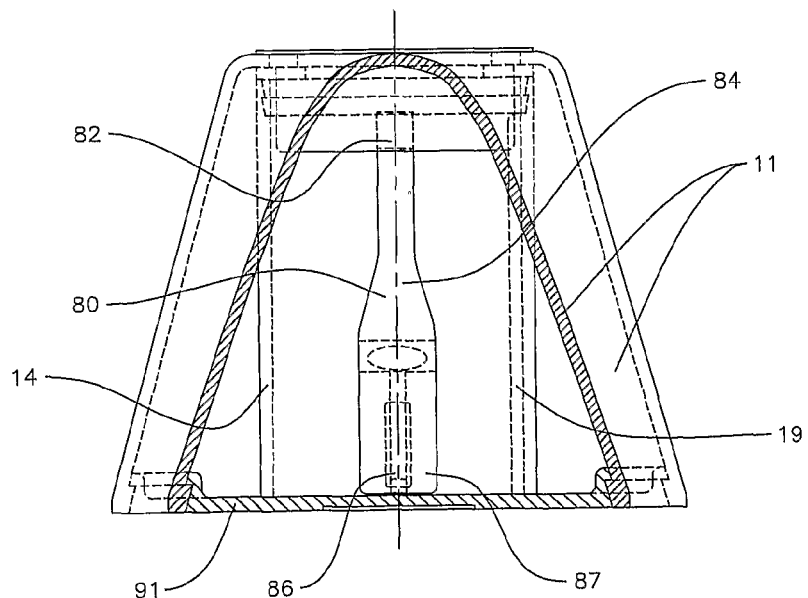
FIG. 6 shows a cross-sectioned elevation view of the housing of FIG. 4 taken through line 6-6.

The illustrated embodiment shown in FIGS. 5, 25 and 27 shows that the release button 81 can have a generally cylindrical shape. The button can have a main inner wall 104 and an annular outer wall 101 having an annular periphery that is slightly larger than the annular opening 102 in the housing body 11 in which the button is disposed. The flared outer wall 101 resist movement of the button 81 into the opening 102 until a manual force is applied that is sufficient to bias inward the outer wall 101. As the button 81 is depressed, it biases elbow 84 of the release arm 80. When the force on the button 81 is released, the resilient elbow 84 will spring back against, and move, button 80 outward to its original position. The button 81 can also provided with a small aperture in its face, through which a small hooked implement can be inserted to pull out the button if it should become lodged inwardly.

To assist in installing the separable attachment assembly 93 to the housing of the device, the lower surface of the housing base 12 can optionally be provided with a wide indent 97 surrounding the opening 95 in the inner base 91, and the separable base 92 can be provided with a raised flange 94 that registers with the indent 97, as shown in FIG. 20. Pressing upward on this area assists engaging the catch 89 onto the latch 96 of the separable base 92.

A top plan view of a typical separable base assembly 93 is shown in FIG. 32, with a sectional view FIG. 33 taken through line 33-33, and detailed sectional views shown in FIGS. 34-35. The adhesive flap 112 extends outwardly from the periphery of the separable base 92, and is covered on its slower surface with the release paper 111. The adhesive flap 112 comprises a first film layer 114 that is affixed on its upper surface to cover the skin-facing surface of the separable base 92, and extends outward from the peripheral circumference of the base 92. The flap 112 has a PSA on its lower surface (not shown) for attachment to the skin. Flap 112 also comprises a second film layer 115 that is shaped as a ring with an inner circular edge 116 and an outer edge 117. The inner edge 116 extends inwardly and is affixed, typically with PSA, to the upper surface of the separable base 92 inboard of its circumferential edge. The second film layer 115 extends outwardly from the separable base 92, to overlap the first film layer 114 to its periphery, and there beyond to its outer edge 117. Typically, the adhesive flap layers 114 and 115 can be made of a flexible plastic film, and can be optionally vapor permeable or breathable.

Alternatively, the second film layer 114 can be eliminated, and the underside of the separable base 92 can have a coating of PSA for direct-contact adhesion to the skin. Optionally a gauze bandage 113 can be secured to the underside of the separable base 92 over the opening 13, as shown in FIG. 35.

In an alternative embodiment, the base securing means and the base separating means can comprise other mechanical securements, an adhesive securement, and a magnetic securement of the separable base to the housing of the device. The other mechanical securements could include a mechanical "hook-and-loop" device that can include Velcro®, a hasp, a frangible joint, and a threaded joint). The magnetic securement can comprise a first magnetic member proximate the upwardly-facing surface of the separable base; and a second magnetic member proximate to the base portion and inside of the housing; wherein first magnet member and the second magnetic member have a magnetic attraction that secures the removable base to the housing, and wherein the removable base can be manually separated from the base portion of the housing by a manually-applied force that overcomes the force of the magnetic attraction.

The separable base provides a means for obtaining a secure attachment of the housing of the device to the patient's skin, by providing for outwardly-extending adhesive flaps that are securely affixed to the relatively rigid structure of the separable base. In most circumstances, the separable base that remains behind on the skin of the patient is well tolerated by the patient, and can be removed at any time, since most vaccinations, particularly with very small needle diameters, leave little wounding of the skin The separable base 92 can also be removed for pre-injection inspection of the device, by fully depressing the release button 81, prior to installing the reservoir or the initiating needle insertion. The inner base 91, or a portion thereof, can be made of a transparent thermoplastic material to allow a visual inspection of the needle and the internal assembly prior to use. The separable base 92 can then be easily reaffixed.

As shown in FIG. 28, after completing the injection, the syringe cartridge 18 can first be removed from the attached housing 10, before the housing is removed from the separable base 92; or, the housing 10 with the syringe cartridge 18 attached can be removed from the separable base 92 as a unit, and then the syringe cartridge can be removed.

Figure 38:
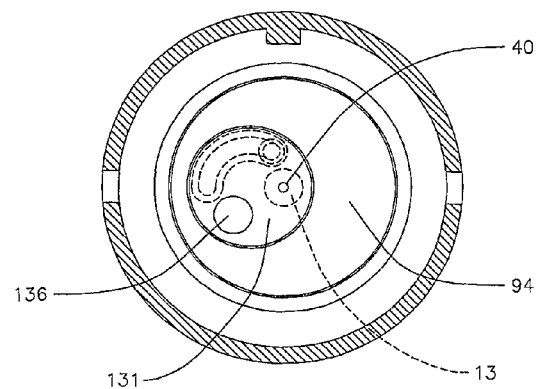
FIG. 38 shows a cross-sectional plan view of the base of FIG. 36, which is in a blocking position to prevent needle deployment.
Figure 36:
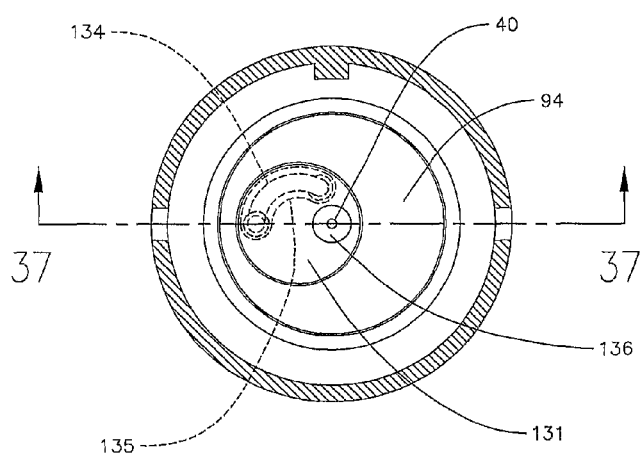
FIG. 36 shows a cross-sectional plan view of a base shown in FIG. 22 through lines 36-36, which has been modified to provide blocking plate that is in a deployment position to allow needle deployment.
Figure 37:
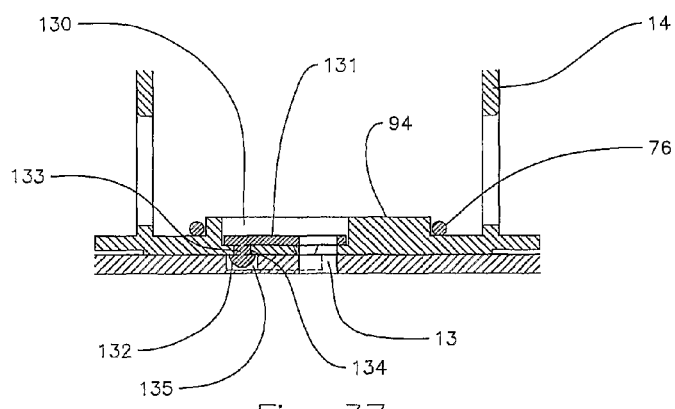
FIG. 37 shows a cross-sectional elevation view of the base of FIG. 36.

The device can also comprise a means for preventing deployment of the needle through the opening in the base of the housing, particularly after the needle has been inside the skin and body of a person. A typical deployment prevention means for preventing needle deployment comprises a sliding or rotating plate disposed in the base that can moved between a first position where the needle opening in the base is not covered by the plate, and a second position wherein the plate covers the opening. In the embodiment illustrated in FIGS. 36-38, a rotating plate 131 is disposed in an annular recess 130 on the annular flange 94 of the inner base 91. The recess 130 and plate 131 have a center that is positioned off the centerline 100 passing through the needle, though they overlap the needle opening 13 in the base 12. The plate 131 has an opening 136 disposed between the center of the plate 131 and its periphery. The plate 131 can rotate between a first deployment position shown in FIGS. 36 and 37 wherein the plate opening 136 registers with and leaves exposed the opening 13, and a second blocking position shown in FIG. 38 wherein the plate 131 covers the opening 13, and prevents deployment of the needle 40. The plate is movable between the first and second positions by a knob 132 that is attached to the plate by a stem 133. The stem is disposed within arc-shaped stem slot 134. The knob 132 moves along a knob recess 135 formed in the inner surface of the removable base 92, and that lies below the knob slot 134. The knob retains the plate in position, and can be manipulated by finger to move the plate between its first and second positions. Prior to injection, the technician can remove the removable base plate and manipulate the knob 132 to move the plate 131 to its deployment position. After the device is removed from the skin following the injection, and the device has been removed from the separable base 92, the exposed knob 132 can be manipulated to move the plate 131 to its blocking position. This physically closes the opening 13 to ensure that the needle 40 can not be redeployed accidentally and cause an undesired stick.

In a second embodiment of the present invention, the device employing a separable base 92 can comprise a device that comprises an on-board power means, as described above, for inserting the injection needle, and optionally, injecting the medication and retracting the needle. As shown in FIG. 19, and referring to FIG. 11, the syringe cavity can comprise a self-contained power source in the form of the compressed pressurizing spring 33. In the illustrated embodiment, the compressed spring is exerting its force upon the vaccine contained in the cavity 66, placing it under pressure. Optionally, in this alternative embodiment, the cylindrical body 31 can be configured with a retainer pin that withholds the pressurizing spring 33 (and therefore pressure upon the vaccine) from contact with the plunger 24, or withholds the plunger 24 itself, until released by a releasing means, such as an annular retaining ring having a tab extending through the cylinder wall 31.

In a third embodiment of the present invention, a device can have a plurality of injection needles and reservoirs disposed within the housing. The device can provide for injecting at least two injectable liquid compositions to a patient. FIGS. 29 and 30 show a top plan view and an elevation view of a device 1 for injecting at least two liquid compositions from separate reservoirs contained in the housing. As shown in FIG. 31, the device 1 can comprise a housing 10 and base 12 for two needle carriages 70a and 70b and two injection needles 40a and 40b, which can be configured to be separately and independently manipulated for insertion, injection and retraction, as described herein above.

Alternatively, the two needle carriages and needles can be configured for simultaneous insertion, injection, and retraction using shared elements, including a shared, dual-recess needle carriage, and a dual unitary pressurizing assembly.

Figure 3A:
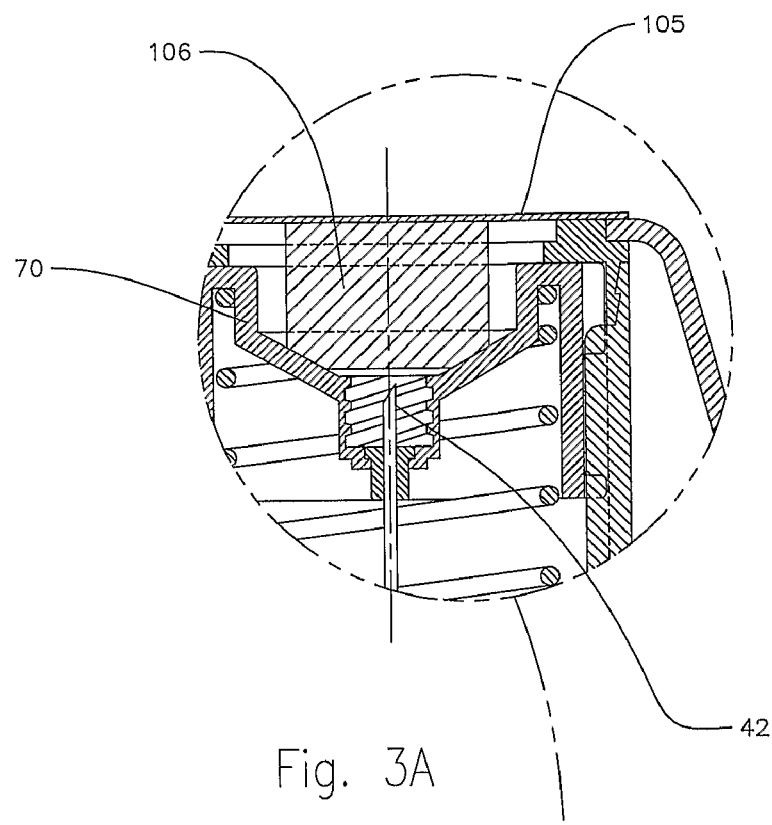
FIG. 3A shows a detailed cross-sectional view of the housing of FIG. 3.
Figure 3:
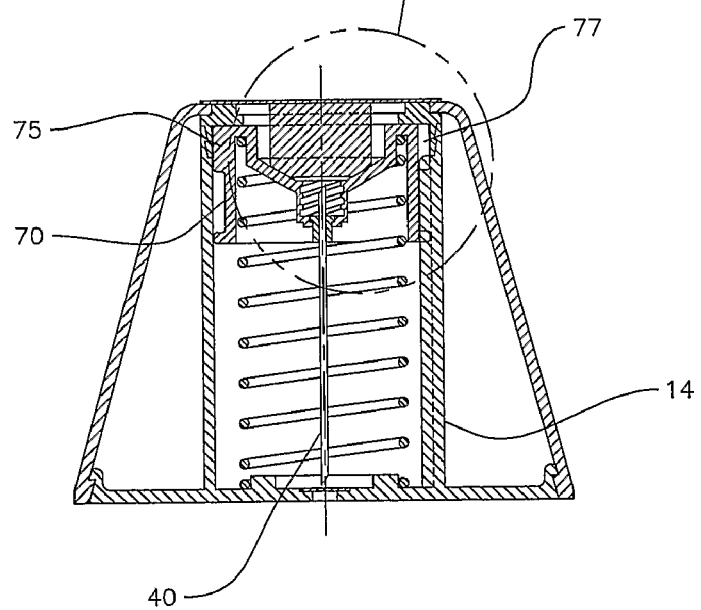
FIG. 3 shows a cross-sectioned elevation view of the housing shown in FIG. 4, taken through line 3-3 of FIG. 4.

If only one injectable liquid composition will be administered, there is a potential for the patient, during the injection procedure, to pick at and possibly poke a finger though the seal 105 that is initially positioned over the cavity recess 71. To prevent this, the seal 105 can be affixed to a cylindrical member 106 that partly supports the underside of the seal 105 layer, as shown in FIG. 3A. Alternatively, the seal can be removed and replaced with a "dummy" plunger that has the upper appearance of the active syringe cartridge, but which fits securely in the opening in the housing above the carriage to block any attempt to depress the carriage.

A further embodiment of the invention can comprise a means of indicating the extent of liquid composition dispensed from the reservoir. The indication means can comprise a visual means that allows personnel to actually view the remaining contents of the reservoir. An embodiment of a visual indication means can comprise a transparent section positioned in a portion of the housing adjacent the reservoir, to view the reservoir. Alternatively, the housing can comprise a door or panel that can be opened to permit inspection. Further, the reservoir can be provided with a corresponding transparent portion to permit the medical personnel to see the medication contained within the reservoir. The transparent portion can include a portion of the base or a portion of the housing, or both. The transparent portion can be a small area relative to the total surface area of the housing body, or can be a significant portion of the housing body surface. In a typical embodiment, the transparent portion is positioned on one side of the housing body that, when applied to the patient's arm, can face away for the patient's line of sight. This allows the medical technician to see through the transparent portion, but provides no indication to the patient, typically a small child, that the inside of the device contains something interesting that might arouse the patient's curiosity.

The indication means can also comprise a signal means that signals the end or the approaching end of medicament dispensing. A signal means can comprise a mechanical or electrical switch that is activated by the plunger member as the last remaining contents of the reservoir is dispensed. The signal can be a flag, a pop-out tab, an illuminated light, or any other well known signal.

Another embodiment of the invention can comprise a covering or disguise configured for attachment or placement over the injection device either to provide the device with a pleasurable impression, or to direct the patient's attention away from the device. The covering can be formed as a cartoon character, a zoo animal, or the like. In this way, much of the patient's fear that might be caused by the sight of the device can be alleviated.

In another embodiment of the invention, the housing of the device can be colored coded or have a colored indicator or marking that identifies the particular type or quantity of medication contained within the reservoir. For example, for one certain medication the outer casing may be blue in color. The device can also display various warnings, such as a precaution to avoid needle stick and possible side effects to the medication. The device can also comprise a removable label comprising information about the liquid composition to be administered (such as the type of vaccine or medicament, the manufacturer and lot number, and volume), which can be placed into a medical record or patient chart.

Another embodiment of the invention, shown in the figures, is an improved injection device for self-administering an injection that does not provide the patient with any convenient fingerhold to grasp the device for jostling or removing the device from the skin during the injection procedure. A preferred design of the device will include an outer surface that has not sharp edges or deep groove with which the patient can get a fingerhold. Preferably, the housing and the base are constructed of a thermoplastic material that has a non-grip or non-sticky surface, and is preferably a resilient material that can flex but not deform in shape. A matte finish on the outside surface can make the housing difficult to grasp, except when properly grasped by a medical technician by its release buttons. Typically, the indentures and grooves in the housing, and including the base, have a breadth not greater than 3 mm, more typically not greater than 1 mm. Typically, external edges can be rounded, maintaining an edge radius of about at least 1 mm, more typically of about at least 3 mm.

While specific embodiments of the apparatus and method of the present invention have been described, it will be apparent to those skilled in the art that various modifications thereto can be made without departing from the spirit and scope of the present invention as defined in the appended claims.

We claim:

1. An injection device for self-administering vaccine injections to a patient, comprising:
    a housing having a base portion; a needle positioned within the housing, the needle having an injection end and having an outside diameter greater than 0.20 mm and less than about 0.38 mm that effects a painless insertion of the needle into the patient, the needle moveable between a first position having its injection end wholly within the housing, and a second position wherein the injection end extends through and beyond the base portion; a reservoir for the vaccine, in liquid communication with the needle; and a means for injecting a vaccine from the reservoir through the needle;
    a separable base associated with the base portion having a skin-facing surface and an opposed surface, the separable base comprising an adhesive on the skin-facing surface that secures the device to the skin of a patient during the time that the device self-administers the injection of the vaccine to the patient, and
    a means for separably securing the separable base with the base portion, and a base separating means for selectively separating the separable base from the device while the separable base is secured to the skin.

2. The device according to claim 1 wherein the separable base can be re-affixed to the base portion after separation.

3. The device according to claim 1 wherein the separable base comprises an adhesive flap extending from a periphery of the separable base, the flap having an adhesive on a skin-facing surface thereof.

4. The device according to claim 3 wherein the adhesive flap extends from the entire periphery of the separable base.

5. The device according to claim 1 wherein the means for separably securing the separable base to the base portion can comprise: a mechanical securement, an adhesive securement, and a magnetic securement, of the separable base with the housing.

6. The device according to claim 1 wherein the means for separably securing comprises at least one engagement in the opposed surface of the separable base; and at least one engaging member extending from the base portion of the housing; wherein the at least one engaging member has a first position associated with the engagement wherein the removable base is secured to the housing, and a second position associated with the engagement wherein the removable base is not secured to the housing.

7. The device according to claim 6 wherein the removable base has a slot in the opposed surface, wherein the at least one engaging member has a latch whereby the latch engages the slot in its first position, thereby securing the seperable base to the housing, and wherein the at least one engaging member can be biased to the second position wherein the latch is not engaged with the slot, thereby unsecuring the separable base to the housing.

8. The device according to claim 7 wherein the at least one engaging member has a button affixed thereto configured to accept a biasing force from outside the housing, which biases the latch of the engaging member to its second, unsecured position.

9. The device according to claim 6, further comprising a means for retracting the needle which retracts the injection end of the needle from its extended position to a position within the housing.

10. The device according to claim 9 wherein the needle retracting means comprises a needle insertion securement having a first position that secures the needle in its extended position, and a second position that does not secure the needle in its extended position, and a power means for biasing the needle toward a position within the housing, whereby when the needle is not secured in its extended position, the needle is retracted to its housing position, and the injection end of the needle is positioned within the housing.

11. The device according to claim 10 wherein the at least one engaging member can not be biased to its second position unless the needle is at its housing position, thereby preventing the injection end of the needle from being extended beyond the base portion of the housing when the separable base is removed from the housing.

12. The device according to claim 1 wherein the self-administering device holds itself in a position attached to the skin of the patient, without requiring a medical technician, the patient, or other person, to hold the device, during the time that the vaccine is injected into the patient through the needle, and wherein the adhesive on the skin-facing surface of the separable base provides adhesive, hands-free, self-attachment of the device to the skin of the patient.

13. The device according to claim 1, wherein the injecting means injects the vaccine at a substantially constant volumetric flow rate of about 0.5 µL/s to about 20 µL/s from the reservoir through the needle, which effects a painless injection.

14. The device according to claim 1, further comprising a means for retracting the needle which retracts the injection end of the needle from its extended position to a position within the housing.

15. The device according to claim 14 further comprising at least one engaging member that can be biased to a second position wherein the removable base is not secured to the housing, wherein the at least one engaging member cannot be biased to its second position unless the needle is at its housing position, which prevents the injection end of the needle from extending beyond the base portion of the housing when the separable base is removed from the housing.

16. An injection device for self-administering vaccine injections to a patient, comprising:

a housing having a base portion; a needle positioned within the housing, the needle having an injection end having an outside diameter greater than 0.20 mm and less than about 0.38 mm, and being configured for extension to a position wherein the injection end extends through and beyond the base portion; a reservoir for the vaccine in liquid communication with the needle; and a means for injecting a vaccine from the reservoir through the needle;

a separable base associated with the base portion having a skin-facing surface and an opposed surface, the separable base comprising an adhesive on the skin-facing surface that secures the device to the skin of a patient during the time that the device self-administers the injection of the vaccine to the patient, a means for separably securing the separable base with the base portion, and a means for retracting the needle, which retracts the injection end of the needle from its extended position to a position within the housing.

17. The device according to claim 16 wherein the needle retracting means separates of the separable base from the separable base portion of the housing after the needle is retracted to its housing position.

18. The device according to claim 16 further comprising a base separating means for selectively separating the separable base from the device while the separable base is secured to the skin.

* * * * *